US012274773B2

(12) United States Patent
Trujillo et al.

(10) Patent No.: US 12,274,773 B2
(45) Date of Patent: Apr. 15, 2025

(54) COSMETIC COMPOSITIONS AND METHODS OF USE

(71) Applicant: K&K BIOTECH, Albuquerque, NM (US)

(72) Inventors: Kristina Trujillo, Placitas, NM (US); Katie Uilk, Albuquerque, NM (US)

(73) Assignee: K&K BIOTECH, Albuquerque, NM (US)

(*) Notice: Subject to any disclaimer, the term of this patent is extended or adjusted under 35 U.S.C. 154(b) by 1125 days.

(21) Appl. No.: 17/011,217

(22) Filed: Sep. 3, 2020

(65) Prior Publication Data

US 2020/0397676 A1    Dec. 24, 2020

Related U.S. Application Data

(63) Continuation of application No. PCT/US2019/063602, filed on Nov. 27, 2019.

(60) Provisional application No. 62/772,856, filed on Nov. 29, 2018.

(51) Int. Cl.
| | |
|---|---|
| *A61K 8/34* | (2006.01) |
| *A61K 8/31* | (2006.01) |
| *A61K 8/35* | (2006.01) |
| *A61K 8/40* | (2006.01) |
| *A61K 8/41* | (2006.01) |
| *A61K 8/81* | (2006.01) |
| *A61K 8/92* | (2006.01) |
| *A61K 8/97* | (2017.01) |
| *A61K 31/055* | (2006.01) |
| *A61K 31/06* | (2006.01) |
| *A61K 36/889* | (2006.01) |
| *A61K 38/00* | (2006.01) |
| *A61P 17/02* | (2006.01) |
| *A61Q 19/08* | (2006.01) |

(52) U.S. Cl.
CPC .............. *A61K 8/347* (2013.01); *A61K 8/315* (2013.01); *A61K 8/35* (2013.01); *A61K 8/40* (2013.01); *A61K 8/418* (2013.01); *A61K 8/8194* (2013.01); *A61K 8/922* (2013.01); *A61K 8/97* (2013.01); *A61K 31/055* (2013.01); *A61K 31/06* (2013.01); *A61K 36/889* (2013.01); *A61K 38/005* (2013.01); *A61P 17/02* (2018.01); *A61Q 19/08* (2013.01); *A61K 2800/591* (2013.01); *A61K 2800/782* (2013.01); *A61K 2800/805* (2013.01)

(58) Field of Classification Search
None
See application file for complete search history.

(56) References Cited

U.S. PATENT DOCUMENTS

| | | |
|---|---|---|
| 8,940,342 B1 | 1/2015 | Johnson |
| 2013/0164393 A1 | 6/2013 | Kaur et al. |
| 2015/0080265 A1 | 3/2015 | Elzinga et al. |

FOREIGN PATENT DOCUMENTS

WO    WO-2015085143 A2 * 6/2015 ............. A61K 31/05

OTHER PUBLICATIONS

Antero Salminen et al., Photoaging: UV radiation-induced inflammation and immunosuppression accelerate the aging process in the skin, Jun. 24, 2022, Inflammation Research, vol. 71, pp. 817-831 (Year: 2022).*
International Search Report and Written Opinion issued on Mar. 18, 2020 in corresponding International Application No. PCT/US2019/063602; 9 pages.
N. K. Zenkov et al., "Keap1/Nrf2/ARE RedoxSensitive Signaling System as a Pharmacological Target", Biochemistry (Moscow), 2013, vol. 17, No. 1, pp. 19-36.
Wollina et al., "Role of adipose tissue in facial aging", Clinical Interventions in Aging, Dove Medical Press Limited, vol. 12, Dec. 6, 2017 pp. 2069-2076.
Gilchrest, "Photoaging", Milestones Cutaneous Biology, Jun. 2013, pp. E2-E6, doi: 10.1038/skinbio.2013.176J, 5 pages.
Asterholm et al., "Adipocyte Inflammation is Essential for Healthy Adipose Tissue Expansion and Remodeling", Cell Metabolism, Cell Press, Elsevier Inc., vol. 20, Jul. 1, 2014, pp. 103-118 with supplemental information, 37 pages.

* cited by examiner

*Primary Examiner* — Nannette Holloman
(74) *Attorney, Agent, or Firm* — Maier & Maier, PLLC

(57) ABSTRACT

The present invention relates to substituted stilbenes and dienones which exhibit unexpected dual activity, as inhibitors of NFκB and as agonists (activators) of Nrf2. In particular, these compounds show dual activity and it has been discovered that these compounds are particularly useful in the treatment of certain cosmetic applications and in rejuvenating and beautifying skin and other keratinous tissue of a subject in need. Cosmetic compositions and methods of using said compositions in combination with other components are disclosed herein.

17 Claims, 27 Drawing Sheets

Scheme 1

FIGURE 2

Table 1
Structures of (E)-stilbenes.[a]

| Product | R₁ | R₂ | Reference[b] | Product | R₁ | R₂ | Reference[b] |
|---|---|---|---|---|---|---|---|
| 1* | 4-OCH₃ | 2-F | 21 | 29* | 4-OCH₃ | 3-F | 2,5-diF | — |
| 2* | — | 2-F | 21 | 30* | 3-F | 3,4-diF | — |
| 3* | — | 3-F | 21 | 31 | 3-F | 2,6-diF | 35 |
| 4* | — | 4-F | 21 | 32 | 3-F | 3-F | 35 |
| 5* | 4-OCH₃ | 3-F | 21 | 33 | 3-F | 4-F | 36 |
| 6* | 4-OCH₃ | 4-F | 21 | 34* | 3-F | 2,5-diF | — |
| 7* | 4-CH₃ | 4-F | 21 | 35* | 3-F | 2,4-diF | — |
| 8 | 4-CH₃ | 3-F | 28 | 36* | 2-F | 2,4-diF | — |
| 9 | 4-CH₃ | 2-F | 28 | 37 | 4-CH₃ | 2,4-diF | 39 |
| 10* | 2-F | 3-OCH₃ | 29 | 38 | 4-F | 3,4-diF | 39 |
| 11 | 3-OCH₃ | 2-F | — | 39 | 4-F | 2,5-diF | — |
| 12 | 3-OCH₃ | 4-F | 29 | 40* | 4-F | 2,3-diOCH₃ | 21 |
| 13 | 3-OCH₃ | 3,4-diOCH₃ | 30 | 41 | — | 3-OCH₃ | 21 |
| 14 | 3-F | 3,4-diOCH₃ | 31 | 42 | 4-OCH₃ | 2,4-diOCH₃ | 21 |
| 15 | 4-F | 2,3-diOCH₃ | 32 | 43 | 4-OCH₃ | 2-Cl | 34 |
| 16 | 3-F | 2,3-diOCH₃ | 33 | 44 | 4-OCH₃ | 3-OH | 40 |
| 17 | 4-F | 2,5-diOCH₃ | — | 45 | 4-OCH₃ | 3-OCH₃, 4-OH | 35 |
| 18* | 4-F | 2-F | — | 46 | 4-CH₃ | 3-CF₃ | — |
| 19 | 4-Cl | 3-F | 29 | 47 | 2,3-diOCH₃ | 4-CH₃ | — |
| 20 | 4-OH | 2,6-diF | 34 | 48* | 3-OCH₃ | 2-OCH₃ | — |
| 21 | — | 3,4-diF | 35 | 49* | 3-OCH₃ | 2,5-diOCH₃ | 41 |
| 22 | 4-CH₃ | 2,5-diF | — | 50* | 4-OCH₃ | 3-NO₂ | 42 |
| 23 | 4-OCH₃ | 3,4-diF | — | 51 | — | 3-NO₂ | 43 |
| 24* | 2-F | 2-F | 36 | 52 | 4-CH₃ | 4-CF₃ | — |
| 25 | 2-F | 3-F | — | 53 | 2,3-diOCH₃ | 4-CH(CH₃)₂ | — |
| 26* | 4-OCH₃ | 3,4-diF | — | 54* | 2,3-diOCH₃ | 2,3-diOCH₃ | — |
| 27 | 2-F | 2-F | 37 | 55* | 2,4-diOCH₃ | 2,5-diOCH₃ | 44 |
| 28 | 4-F | 3-F | 38 | 56 | | | |

[a] Data for starred compounds is reported in the experimental section.
[b] Melting points and NMR data of known compounds are in agreement with the literature data.

FIGURE 3

Table 2. Activation of Nrf2 by mono-fluoro *trans* stilbenes

| Number | Structure | EC$_{50}$ (μM) | Fold activation |
|---|---|---|---|
| Sulforaphane | 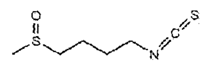 | 1.2 ± 0.08 | 12.4 |
| Resveratrol | 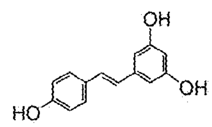 | 5.4 ± 0.5 | 3.2 |
| 1 (LD55) | 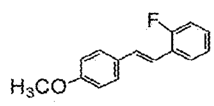 | 5.4 ± 0.3 | 14.9 |
| 2 | 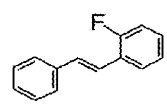 | 0.7 ± 0.1 | 10.7 |
| 3 | 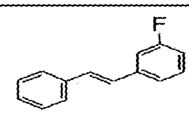 | 3.1 ± 0.4 | 4.9 |
| 4 | 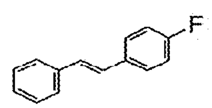 | 12.4 ± 0.5 | 4.8 |
| 5 | 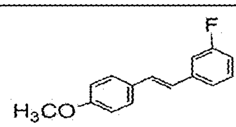 | 8.9 ± 0.9 | 3.6 |
| 6 | 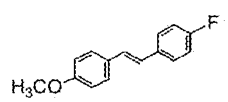 | 4.2 ± 0.4 | 1.7 |
| 7 | 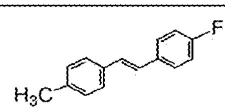 | 1.3 ± 0.2 | 1.1 |
| 8 | 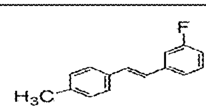 | 0.8 ± 0.08 | 4.7 |
| 9 | 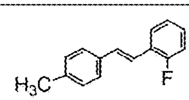 | 1.4 ± 0.2 | 10.1 |
| 10 | 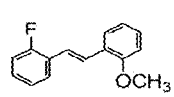 | 3.1 ± 0.2 | 18.4 |

FIGURE 3 (Cont'd)

| Number | Structure | EC$_{50}$ (µM) | Fold activation |
|---|---|---|---|
| 11 | 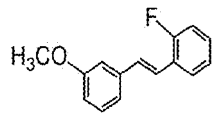 | 3.8 ± 0.2 | 14.4 |
| 12 | 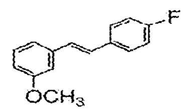 | 6.0 ± 0.5 | 4.4 |
| 13 | 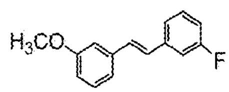 | 2.3 ± 0.5 | 15.1 |
| 14 | 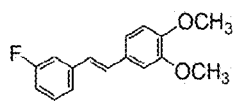 | 9.5 ± 0.7 | 5.9 |
| 15 | 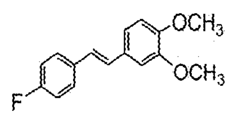 | 2.6 ± 0.5 | 1.6 |
| 16 | 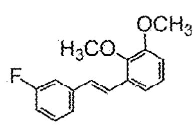 | 1.9 ± 0.1 | 19.4 |
| 17 | 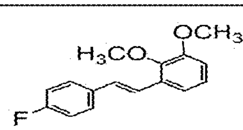 | 2.9 ± 0.1 | 16.9 |
| 18 | 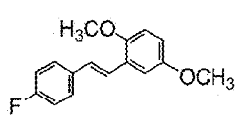 | 5.1 ± 0.5 | 10.7 |
| 19 | 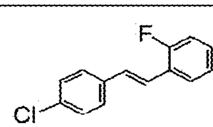 | 1.6 ± 0.2 | 5.3 |
| 20 | 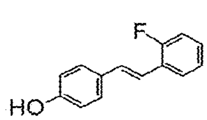 | 11.4 ± 1.6 | 13.4 |

FIGURE 4
Table 3. Activation of Nrf2 by polyfluoro *trans* stilbenes
| Number | Structure | EC$_{50}$ (µM) | Fold activation |
|---|---|---|---|
| 21 | 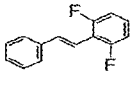 | 6.9 ± 0.1 | 11.4 ± 0.4 |
| 22 | 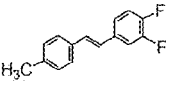 | 2.6 ± 0.18 | 10.2 ± 0.2 |
| 23 | 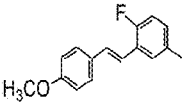 | 3.2 ± 0.5 | 17.0 ± 0.9 |
| 24 | 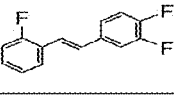 | >15 | 11.5 ± 2.0[a] |
| 25 | 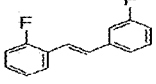 | >15 | 8.5 ± 0.2[a] |
| 26 | 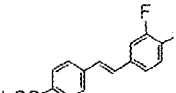 | >15 | 4.6 ± 0.6[a] |
| 27 | 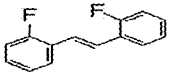 | 4.3 ± 0.4 | 13.9 ± 0.9 |
| 28 | 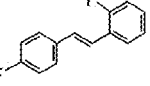 | 3.6 ± 0.3 | 12.7 ± 0.4 |
| 29 | 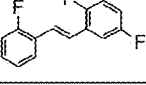 | 5.9 ± 0.2 | 22.3 ± 0.5 |
| 30 | 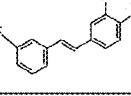 | 5.0 ± 0.1 | 12.2 ± 0.8 |
| 31 | 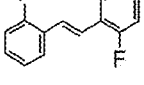 | 1.4 ± 0.5 | 21.2 ± 2.0 |

FIGURE 4 (Cont'd)
Table 3 (Cont'd)
| Number | Structure | EC$_{50}$ (μM) | Fold activation |
|---|---|---|---|
| 32 | 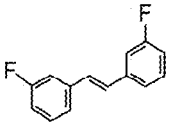 | 1.0 ± 0.12 | 7.0 ± 0.7 |
| 33 | 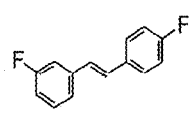 | 0.65 ± 0.12 | 4.5 ± 0.4 |
| 34 | 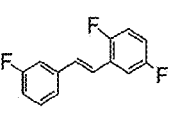 | 0.3 ± 0.02 | 10.7 ± 1.0 |
| 35 | 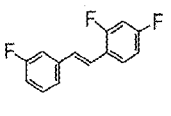 | 0.45 ± 0.01 | 8.2 ± 0.2 |
| 36 | 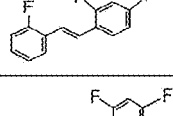 | 9.6 ± 0.14 | 5.0 ± 0.8 |
| 37 | 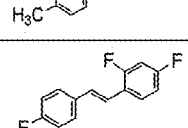 | 2.0 ± 0.07 | 13.5 ± 0.2 |
| 38 | 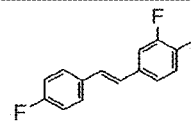 | 0.9 ± 0.08 | 16.8 ± 1.8 |
| 39 | 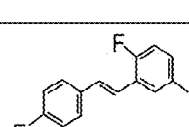 | >15 | 7.0 ± 0.5[a] |
| 40 | 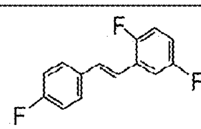 | 2.9 ± 0.59 | 11.2 ± 0.1 |

FIGURE 5

Table 4. Activation of Nrf2 by non-fluoro *trans* stilbenes

| Number | Structure | EC$_{50}$ (µM) | Fold activation |
|---|---|---|---|
| 41 | 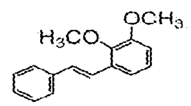 | 4.7 ± 0.7 | 25.4 |
| 42 | 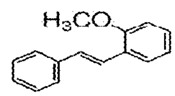 | 4.4 ± 0.1 | 23.1 |
| 43 | 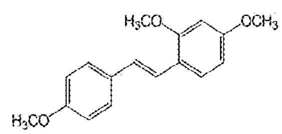 | 4.6 ± 0.4 | 15.6 |
| 44 | 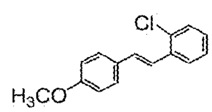 | 3.1 ± 0.2 | 17.8 |
| 45 | 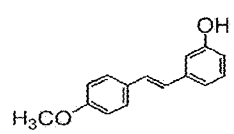 | >15 | 28.1 |
| 46 | 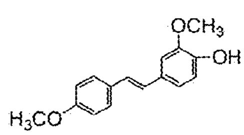 | 3.7 ± 0.5 | 27.7 |
| 47 | 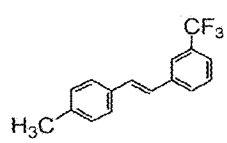 | 1.5 ± 0.5 | 19.2 |
| 48 | 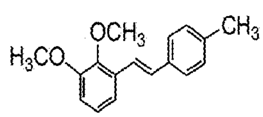 | 1.1 ± 0.2 | 16.1 |
| 49 | 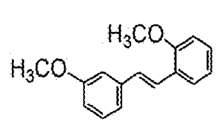 | 4.4 ± 0.2 | 29.2 |

FIGURE 5 (Cont'd)
Table 5 (Cont'd)
| | | | |
|---|---|---|---|
| 50 | 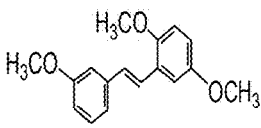 | >15 | 15.7 |
| 51 | 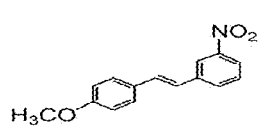 | 3.3 ± 0.4 | 69.0 |
| 52 | 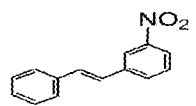 | 3.0 ± 0.4 | 18.6 |
| 53 | 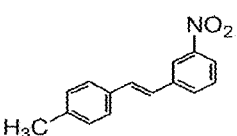 | 3.7 ± 0.2 | 11.9 |
| 54 | 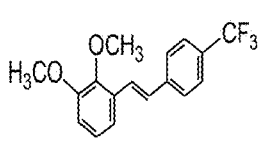 | 2.2 ± 0.1 | 65.5 |
| 55 | 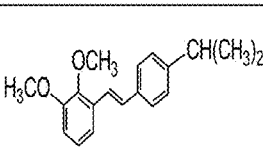 | 2.7 ± 0.3 | 33.9 |
| 56 | 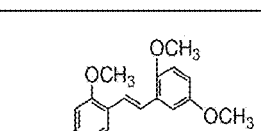 | 0.8 ± 0.03 | 12.9 |

FIGURE 6
EC$_{50}$ values for inhibition of NF-κB and activation of Nrf2 by resveratrol analogues (trans stilbenes) and by curcumin analogues (dienones)
| Compound | Structure | EC$_{50}$ (μM) NFkB | EC$_{50}$ (μM) Nrf2 |
|---|---|---|---|
| Resveratrol | 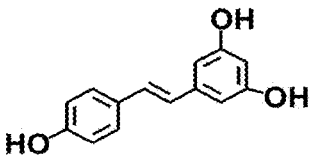 | 20 ± 3 | 5.4±0.5 |
| Curcumin | 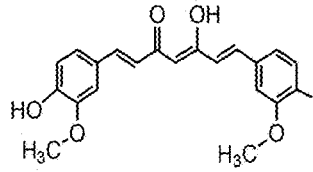 | 8.2±0.4 | 21±0.02 |
| 1 (LD55) | 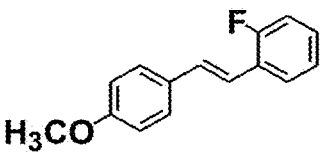 | 0.15 ± 0.1 | 5.4±0.3 |
| 5 | 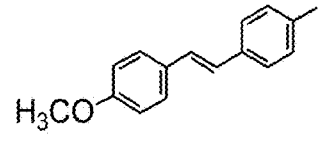 | 1.1±0.6 | 8.9±0.9 |
| 6 | 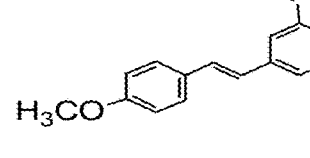 | 3-5 | 4.2±0.4 |
| 7 | 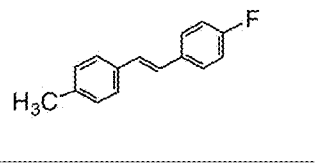 | 3-5 | 1.3±0.2 |
| 8 | 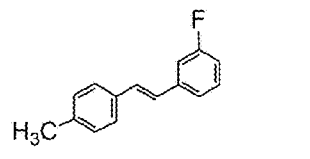 | 0.77±0.3 | 0.8±0.08 |

FIGURE 6 (Cont'd)
Table 6 Continued
| Compound | Structure | EC$_{50}$ (μM) NFkB | EC$_{50}$ (μM) Nrf2 |
|---|---|---|---|
| 9 | 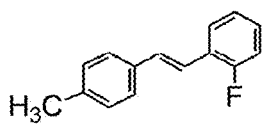 | 0.63±0.5 | 1.4±0.2 |
| 11 | 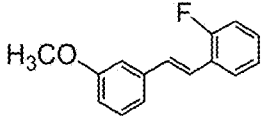 | 3 - 5 | 3.8±0.2 |
| 12 | 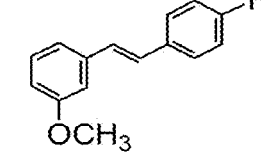 | 3 - 5 | 6.0±0.5 |
| 44 | 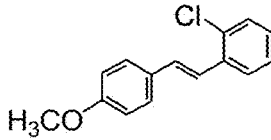 | 1.5±0.03 | 3.1±0.2 |
| dienone analogue of curcumin | 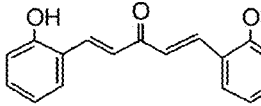 | 4.1±0.3 | 3.3±0.5 |
| Dienone analogue | 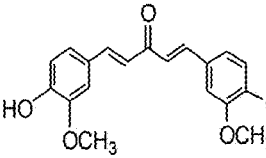 | 9.6±0.7 | 9.9±0.6 |

WRINKLES
Non-Treated
Treated side
45 days treatment
Treated side
90 days treatment
FIGURE 7

FIGURE 8
Mirrored image of Treated side 45 days
Mirrored image of non-treated side FIGURE 9
WRINKLES
Non-Treated side
Treated side
14 days
treatment
Treated side
28 days
treatment FIGURE 10
90 Days treatment-
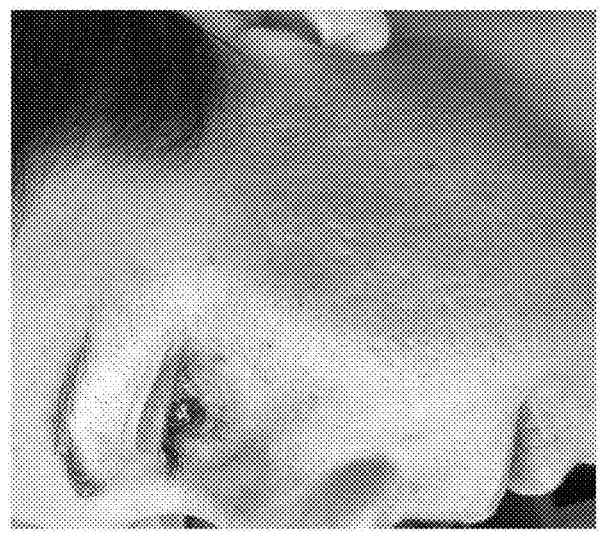
45 Days treatment-
Non-Treated
Acne scars FIGURE 11
Treated- 14 days
Non-Treated
WRINKLES

FIGURE 13
Skin smoothing and beautification
Before
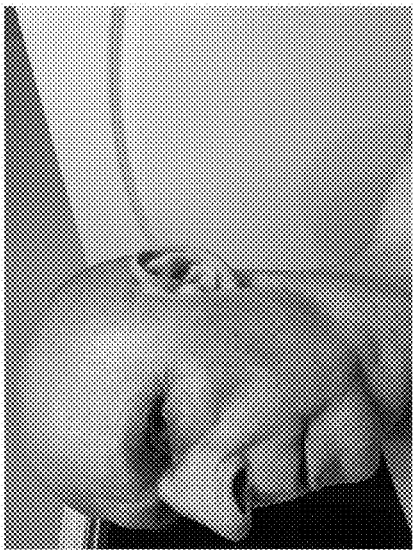
After- 49 days treatment
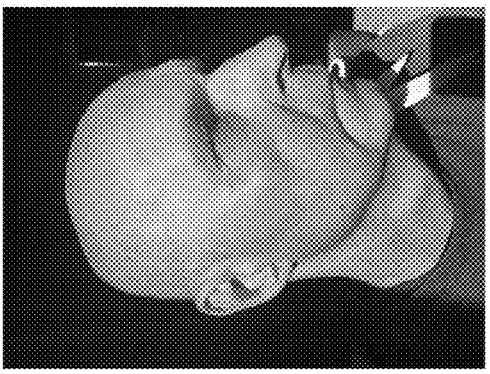

Skin smoothing and beautification

Stretch Marks and skin tightness on the stomach

FIGURE 17
Stretch Marks on the stomach
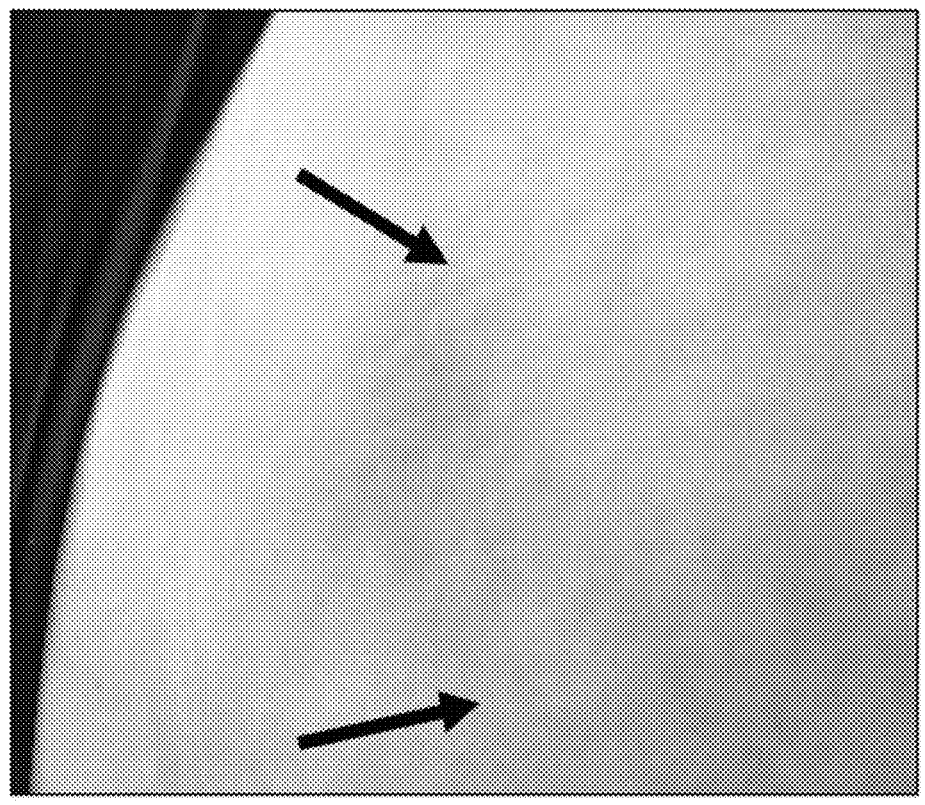
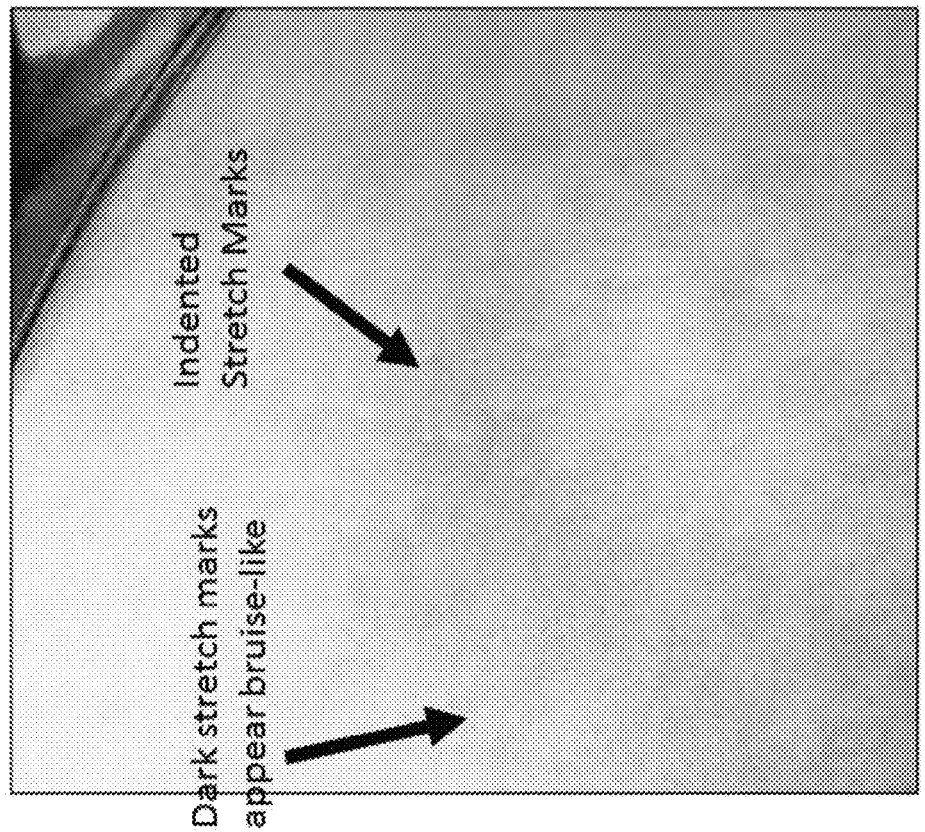
AFTER
BEFORE

Stretch Marks on the stomach

FIGURE 20
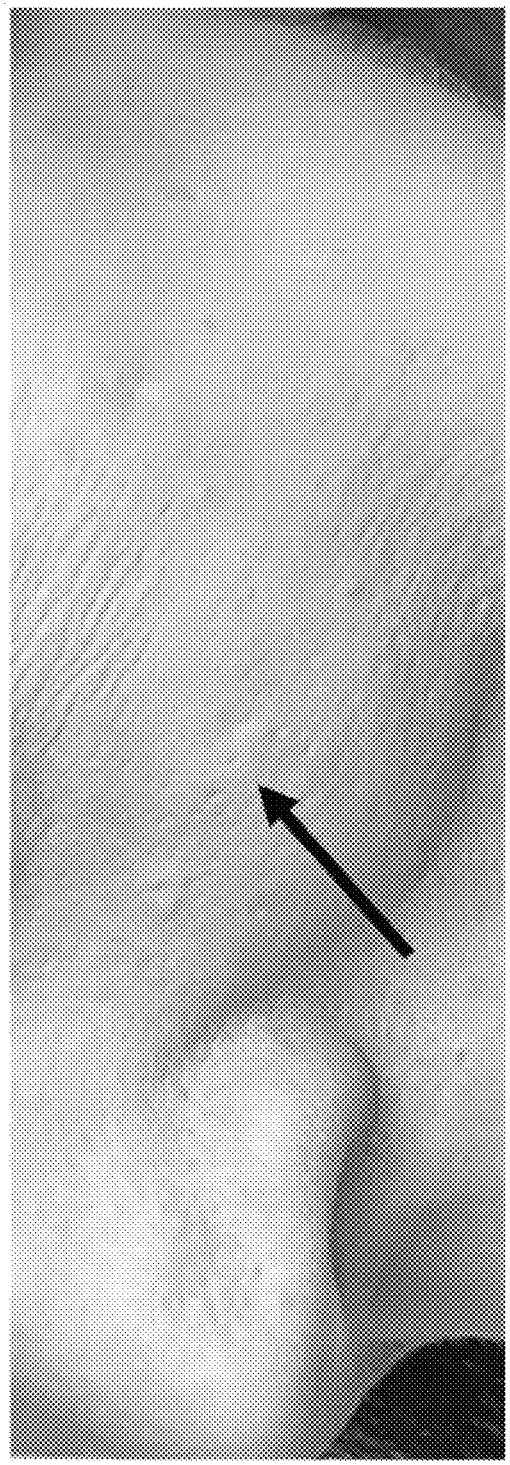
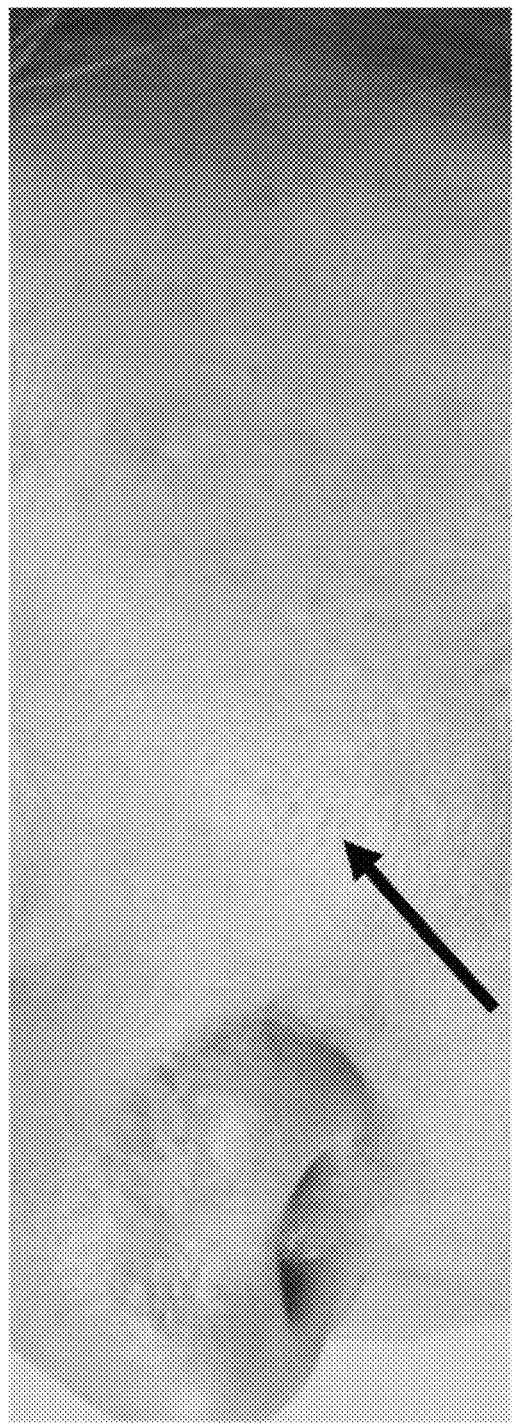

FIGURE 22 Acne scar/redness

FIGURE 23
Overall Skin Rejuvenation
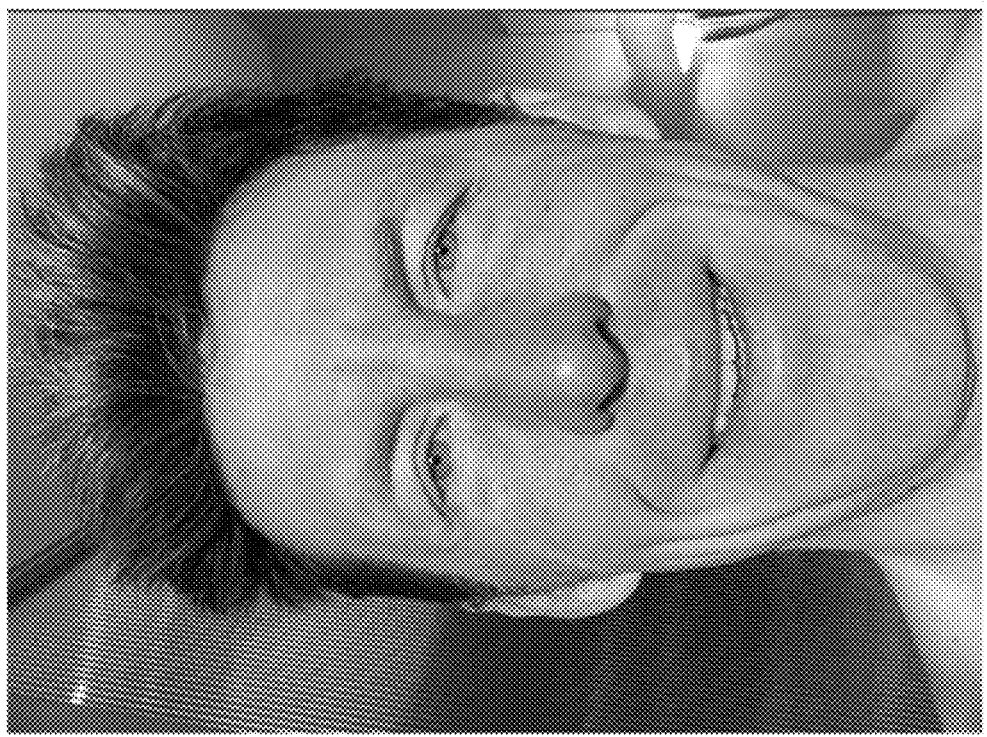
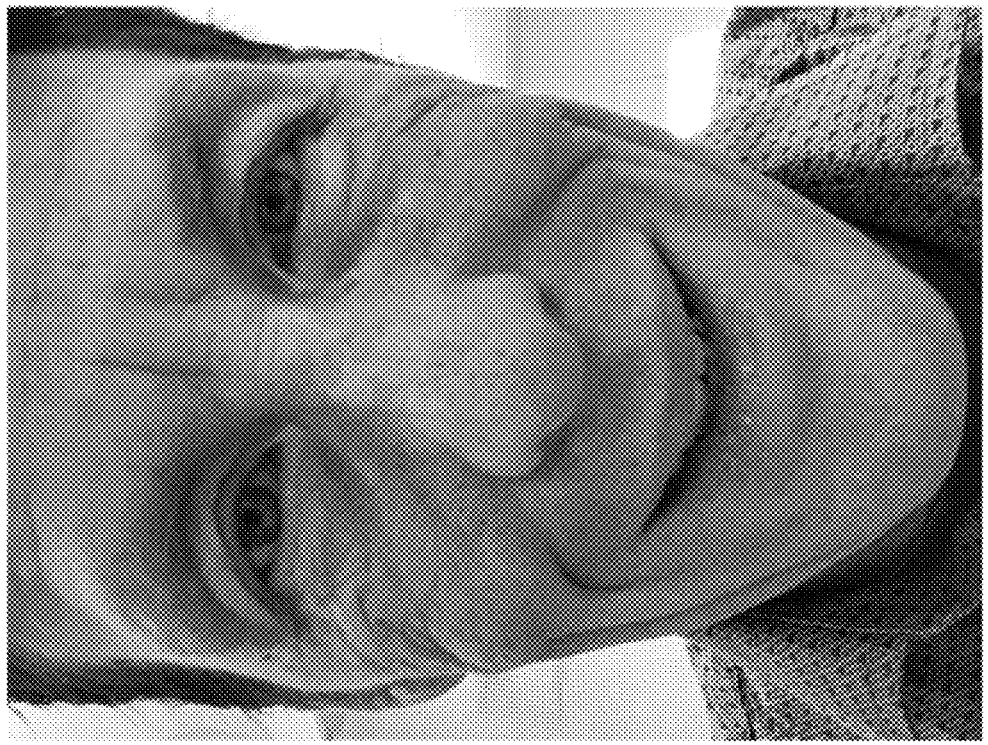

COSMETIC COMPOSITIONS AND METHODS OF USE

CROSS-REFERENCE TO RELATED APPLICATIONS

This application is a continuation of International application No. PCT/US2019/63602, filed Nov. 27, 2019, which claims the benefit of priority of U.S. provisional application No. 62/772,856, filed Nov. 29, 2019, the entire contents of which are incorporated by reference herein.

FIELD

The present invention relates to substituted stilbenes and dienones which exhibit unexpected activity, as inhibitors of proinflammatory NFκB signaling and as agonists (activators) of anti-oxidant Nrf2 signaling. In particular, these compounds show dual anti-inflammatory activity and anti-oxidant activity as well as unique cosmetic activity in the treatment, repair, rejuvenation and beautification of the skin and keratinous tissue of a subject, including enhancing skin elasticity, which makes them particularly useful in the treatment of certain cosmetic conditions, especially treating wrinkles/wrinkled skin and cellulite, acne scars, other scars that won't heal, stretch marks, rashes, repairing damaged skin, smoothing rough skin, reducing and/or eliminating warts and other skin imperfections, naturalizing skin color to its original condition and treating damaged skin and rashes from poison ivy and poison oak and other environmental insults, as well as beautifying and rejuvenating skin. Compositions (both cosmetic and pharmaceutical) and methods of treatment, including methods of treating and beautifying the skin are described herein.

BACKGROUND

The nuclear factor κB (NF-κBa) family of transcription factors in mammals consists of homo- and heterodimeric combinations of five related proteins (p50, p52, p65/RelA, c-Rel, and RelB) that have a marked influence on the expression of numerous genes involved in immunity and inflammation, as well as cellular stress responses, growth, and apoptosis. Diverse pathways activate NF-κB, and control of these pathways is increasingly viewed as an approach to chemotherapy in the many diseases that have an associated inflammatory component, including cancer, stroke, Alzheimer's disease, and diabetes. Activation of NF-κB occurs through multiple pathways.

Transcription factor nuclear factor erythroid 2 related factor 2 (Nrf2), which is a member of the cap'n' collar family of transcription factors, is the master regulator of an inducible cellular system of cytoprotective genes. These genes code for a broad range of proteins, including phase I and II detoxification enzymes, anti-oxidant proteins, as well as anti-inflammatory and neuroprotective factors, growth factors and receptors, and other transcription factors. Interest has emerged in Nrf2 as a therapeutic target, especially for treatment of chronic inflammatory diseases and the associated oxidative stress.

Numerous Nrf2-activating chemicals have been identified, including some natural product phenols, such as the enone curcumin and the trans stilbene resveratrol, that can activate Nrf2 after oxidation to electrophilic quinones, which can modify select cysteine residues in Keap1 by Michael addition. Keap1 cysteine residues 273, 288 and 151 appear to be especially important. Peptide inhibitors of the Keap1-Nrf2 protein-protein interaction have been developed as well as a variety of small molecules that inhibit the Keap1-Nrf2 interaction. These studies have been aided by the availability of several crystal structures of Nrf2.[20-22]

Natural product phenols such as curcumin and resveratrol exhibits numerous biological activities including ability to induce the expression of Nrf2-dependent phase II and antioxidant enzymes such as glutathione S-transferase, aldose reductase and heme oxygenase-1. Curcumin appears to utilize more than a single mechanism for activation of Nrf2, including covalent modification of Keap1 and activation of upstream kinases. Curcumin has been examined in a number of clinical studies with limited success, mainly owing to limited bioavailability and rapid metabolism. Attempts to improve curcumin as a therapeutic agent include development of new formulations that may enhance bioavailability.

There is considerable interest in the development of analogues and derivatives of natural product phenols with improved therapeutic potential.[29-32] There also is interest in the development of analogues that activate anti-oxidant Nrf2 but simultaneously inhibit proinflammatory NF-κB signaling,[33-35] which is consistent with the ability of curcumin and resveratrol to target both of these pathways.[36,37] In the present application is a description and evaluation of trans stilbene analogues of resveratrol as well as dienone analogues of curcumin for use in cosmetic applications, which have to date, not been studied. It has unexpectedly been discovered that these compounds exhibit biological activity consistent with unique cosmetic activities as otherwise described herein.

SUMMARY

The present invention is directed to the use of compounds, exhibiting both the simultaneous inhibition of NF-κB pathway and activation of the Nrf2 pathway for cosmetic applications which have not been previously investigated or studied. Pursuant to this thesis, it has been unexpectedly discovered that compositions comprising at least one compound which exhibits a dual activity inhibition of NF-κB pathway and activation of the Nrf2 pathway are particularly useful for beautifying and rejuvenating skin by enhancing the appearance of skin and for treating wrinkles, acne scars and other scars, repairing damaged skin, including skin which has been damaged from shaving (including razor burns and cuts), smoothing rough skin, reducing and/or eliminating warts and other skin imperfections, naturalizing skin color to its original condition and treating damaged skin from poison ivy, poison oak and other environmental insults.

In one embodiment, the present invention is directed to compositions for use in beautifying and/or rejuvenating skin and/or in inhibiting, reducing or alleviating wrinkles, acne scars other scars of the skin, repairing damaged skin, hair and nails (keratinous tissue including ungula tissue), including skin which has been damaged from shaving (including razor burns, cuts and rashes), aging, sun damage, environmental toxins, stress and poor diet, smoothing rough skin, reducing and/or eliminating warts and other skin imperfections, naturalizing skin color to its original condition and treating damaged skin and rashes from poison ivy, poison oak and other environmental insults, which comprise an effective amount of at least one compound according to the chemical structure which appears below. Compositions according to the present invention are also effective to beautify skin, i.e., substantially enhance the appearance of skin of a subject desirous or in need of such a result. All of these compounds exhibit dual activity as inhibitors (down regulators) of the NF-κB pathway and agonists (up-regulators) of the Nrf2 pathway.
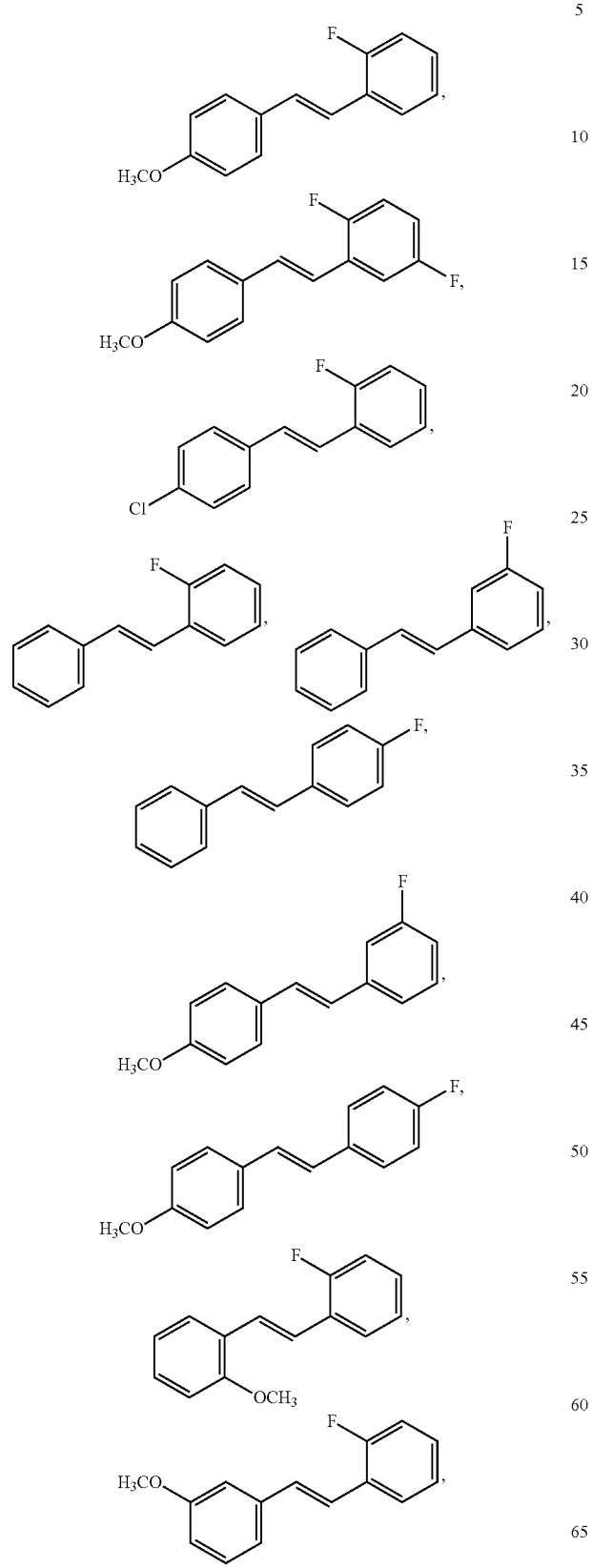
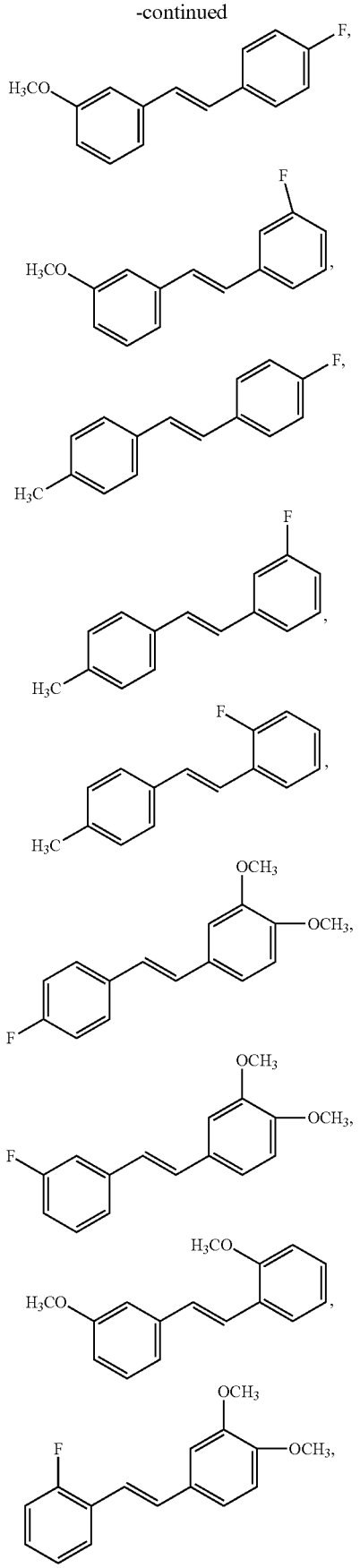

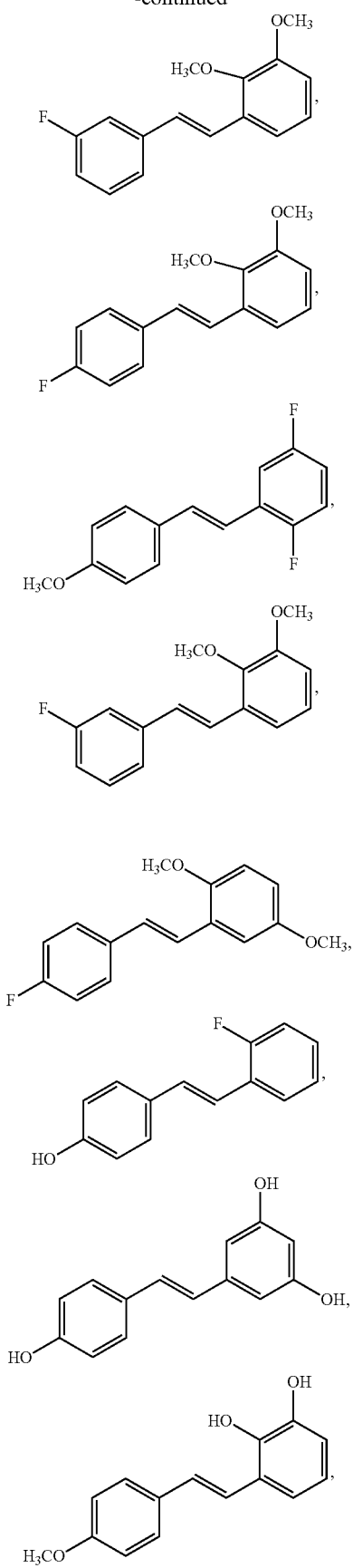
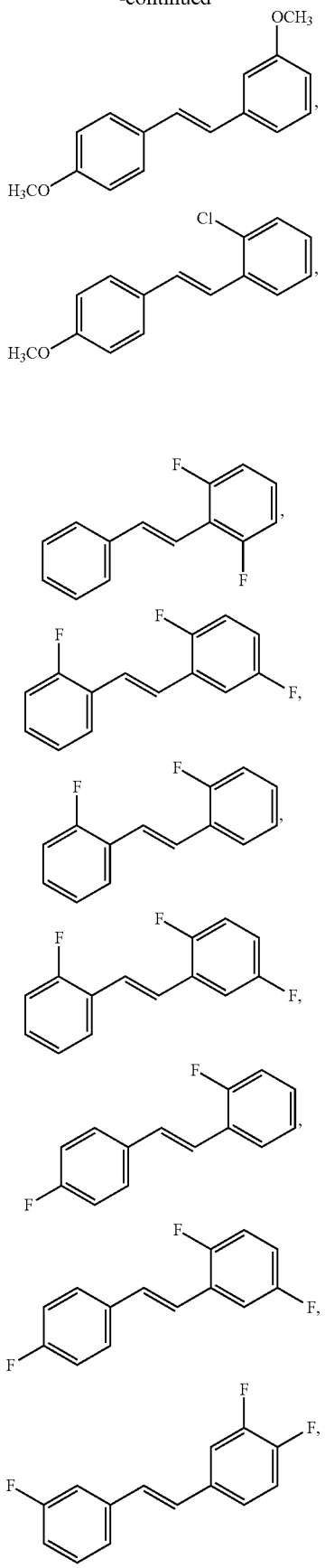

-continued
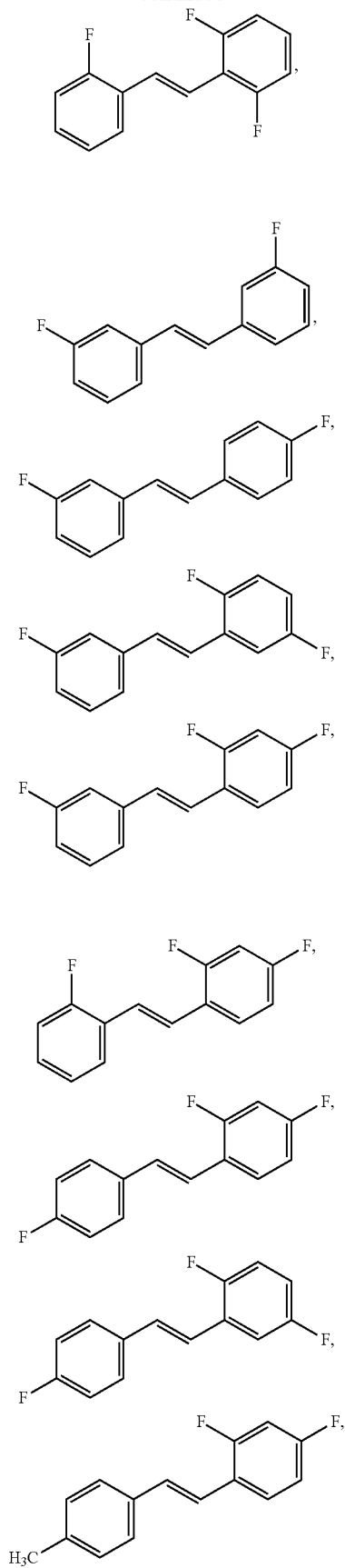
-continued
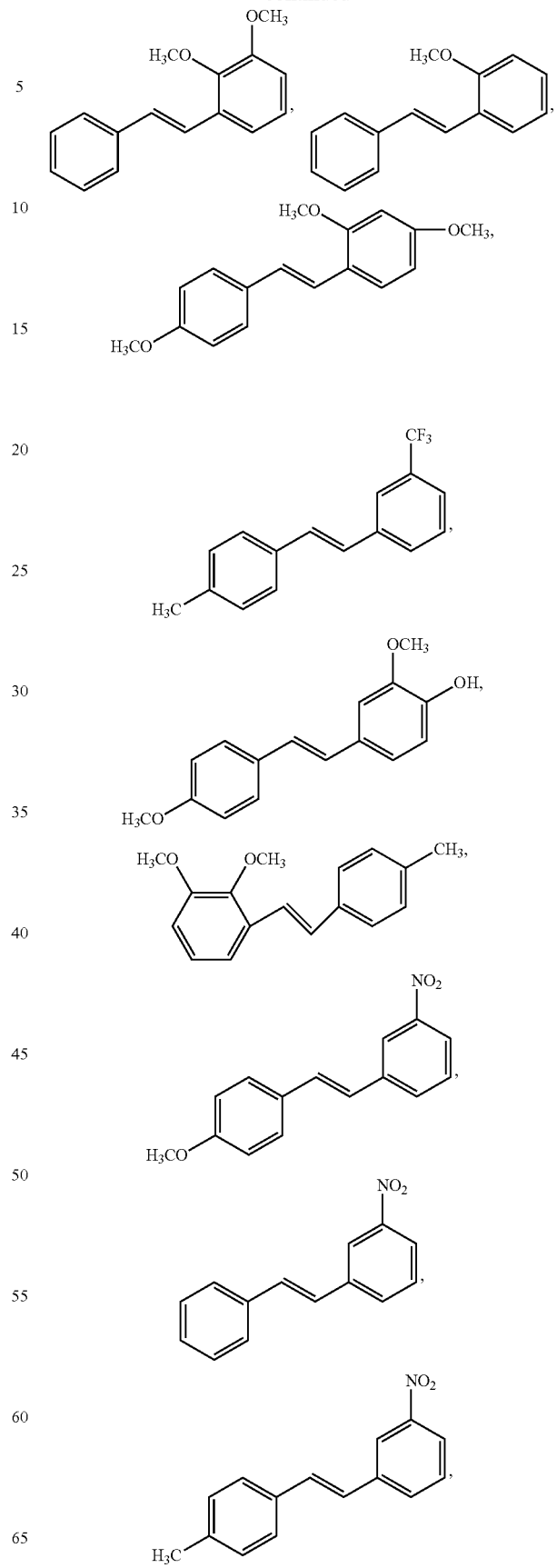

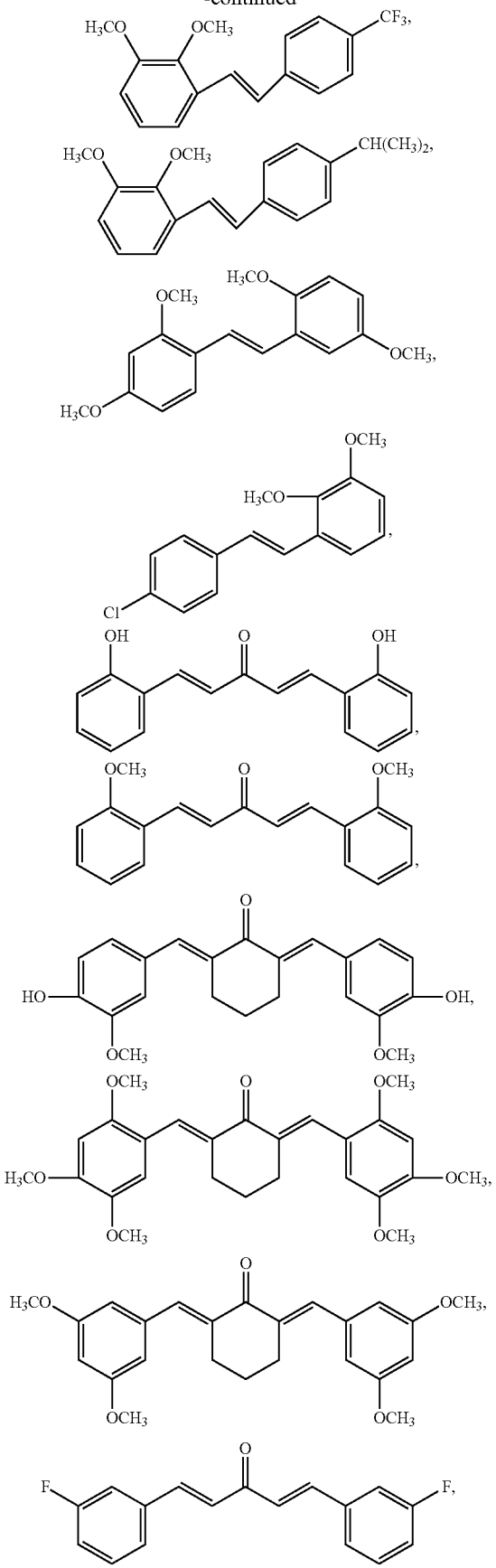
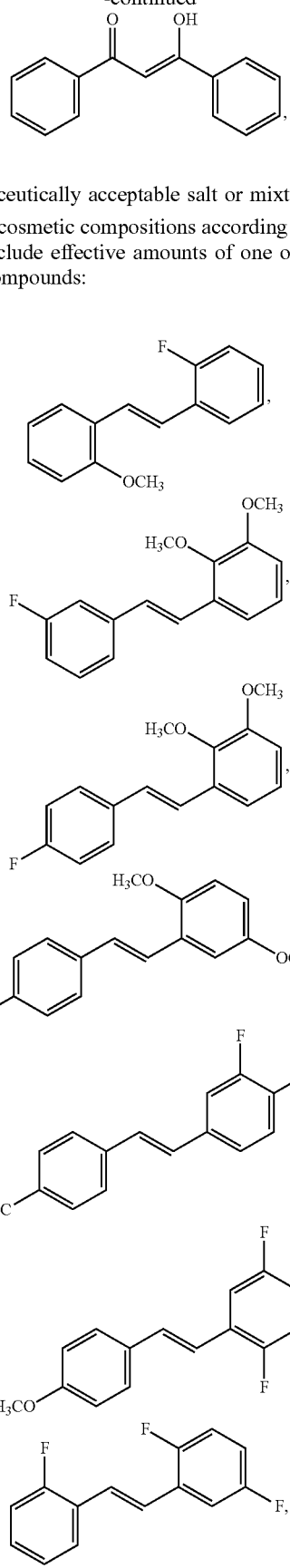
or a pharmaceutically acceptable salt or mixture thereof.
Preferred cosmetic compositions according to the present invention include effective amounts of one or more of the following compounds:

-continued
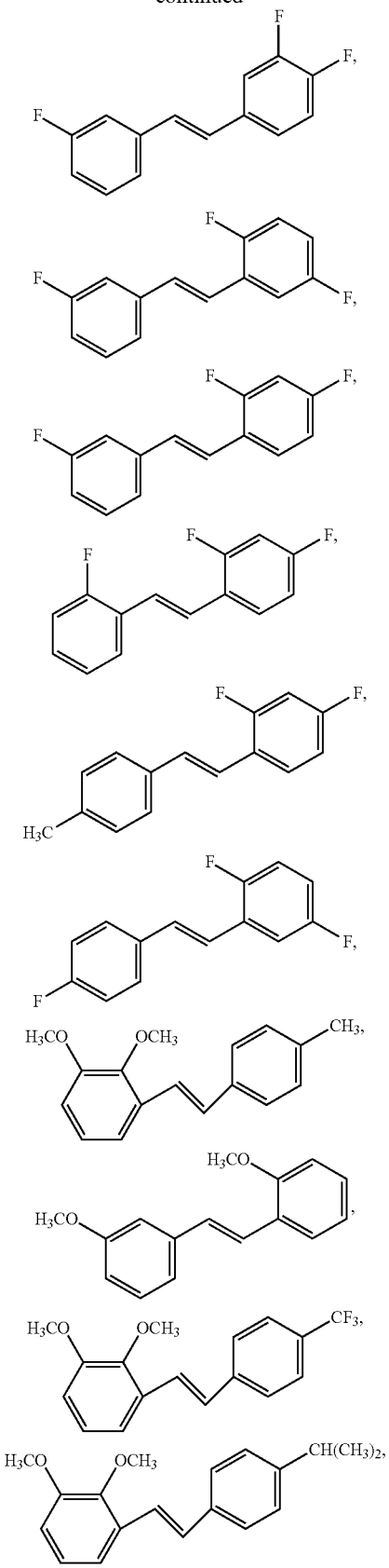
or a pharmaceutically acceptable salt thereof.
In alternative embodiments, preferred compositions include one or more of the following compounds in an effective amount:
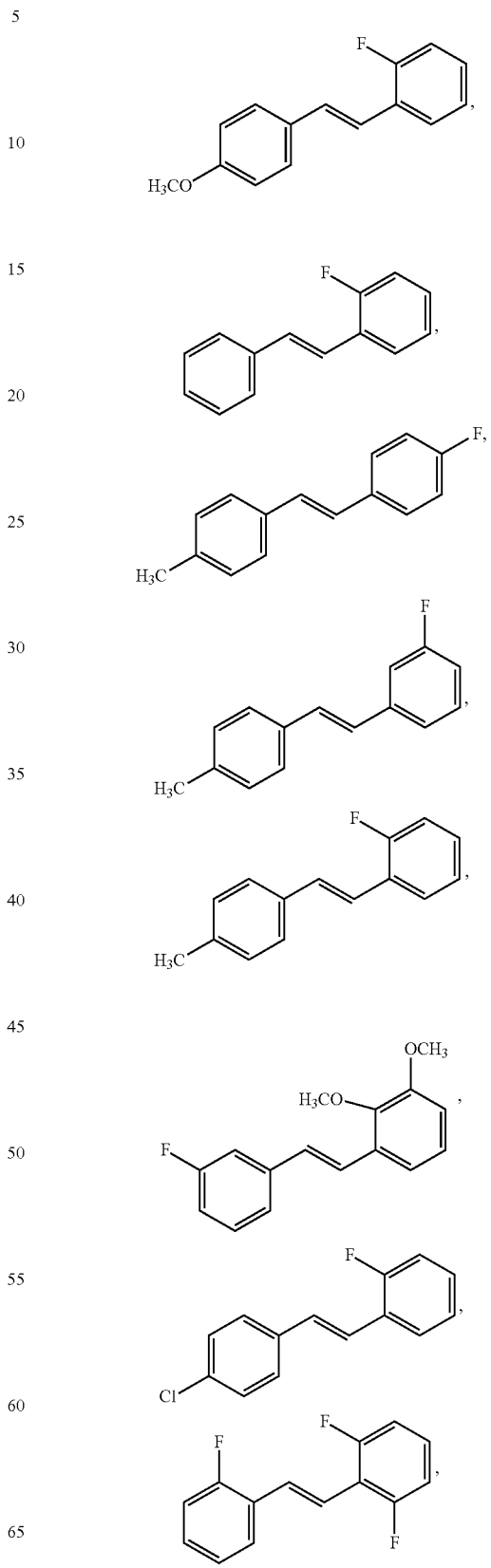

-continued

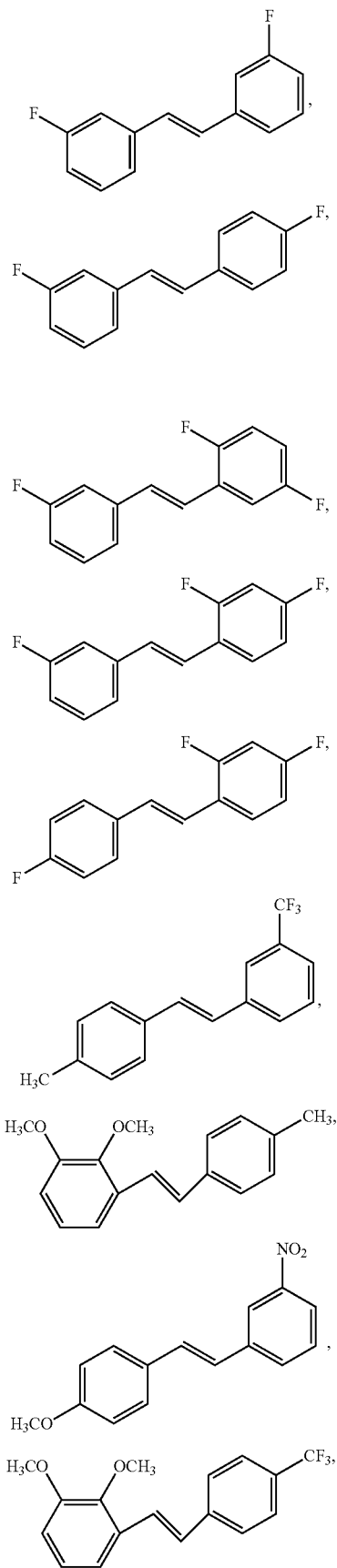

-continued

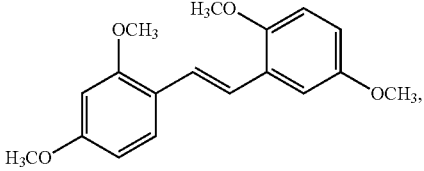

or a pharmaceutically acceptable salt thereof.

In another embodiment, the present invention relates to cosmetic (topical) compositions comprising an effective amount of at least one compound according to the chemical structure set forth above in combination with at least one additional cosmetic additive selected from water, a water compatible cosmetically acceptable solvent such as alcohol, a water incompatible solvent, emollients, humectants, oils (polar and non-polar which may provide oil-in-water or water-in-oil emulsions, an essential oil such as lavender, *Melaleuca*, peppermint, frankincense, *eucalyptus*, among others, which include penetration enhancing terpenes such as α-pinene, β-pinene, camphene, β-myrcene, δ-3-carene, α-terpinene, cis-ocimene, limonene, p-cymene, trans-ocimene, γ-terpinene, terpinolene, linalool, geraniol, β-caryophyllene, cis-nerolidol, trans-nerolidol and mixtures thereof, each of which may be included as separate individual components in compositions according to the present invention), conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, preservatives and mixtures thereof, among others. Compositions according to the present invention also optionally include an additional bioactive agent, such as an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, antibiotics (e.g. tetracyclines including doxycycline, limecycline and minocycline; clindamycin, erythromycin, trimethoprime and cotrimoxazole, or a mixture thereof, among others), pharmaceutically acceptable salts and esters thereof and the like and mixtures thereof, among others, vitamins, especially including vitamin C, vitamin E, vitamin A, coenzyme Q, aloe vera and other agents which are useful to enhance the appearance of skin. In certain embodiments, cosmetic compositions comprise at least two of the above-described compounds.

Particularly preferred additives/components for use in the present cosmetic compositions along with the active stilbene/dienone compound are selected from the group consisting of essential oils such as lavender, *melaleuca*, peppermint, frankincense, rosemary, *eucalyptus*, elderberry, cucumber and watermelon; oils such as argan oil and grape seed oil; seed fats such as shea butter and almond oil and natural wax such as bees wax and mixtures thereof.

The results achieved with stilbenes and or dienones (and especially LD55) in the blend of carrier and essential oils were unexpected and synergistic due to the combination of ingredients, as opposed to the effects of each ingredient on its own (additive). The combination in compositions according to the present invention provides unexpected synergistic activity for the following reasons.

1. Solubility—The stilbenes/dienones according to the invention, especially LD55, are hydrophobic and require oil-based carriers in order to dissolve and be absorbed into the skin;

2. Skin penetration enhancers—The specific combination of oils includes several essential oils which contain high levels of terpenes. Terpenes are well known to significantly increase the permeability of the skin, and have been extensively investigated as drug delivery enhancers. These benefit the compositions according to the present invention by synergistically enhancing activity of the compositions.
3. Synergistic anti-inflammatory pathways—stilbenes/dienones according to the present invention, especially LD55, exert anti-inflammatory effects primarily through inhibition of the NF-KappaB pathway. The carrier oils used in the blend also have anti-inflammatory properties, however the mechanism of action works through different biological pathways. Therefore, the specific blend is required to maximize the anti-inflammatory properties, resulting in the unexpected effects of the blend.
4. Synergistic anti-oxidant pathways. Stilbenes/dienones according to the present invention, especially LD55, exert anti-oxidant effects primarily through activation of NFR2. The carrier oils used in the blend also have anti-oxidant properties, however the mechanism of action works through different biological pathways. Therefore, the specific blend is required to maximize the anti-oxidant properties, resulting in the unexpected effects of the blend.

In still another embodiment, the present invention is directed to a method for rejuvenating and/or beautifying the skin and improving skin elasticity, or otherwise treating, inhibiting, reducing or alleviating wrinkles, acne scars and other scars of the skin and keratinous tissue that won't heal, stretch marks, repairing damaged skin, hair and nails (keratinous tissue including ungual tissue), including skin which has been damaged from shaving (including razor burns, cuts and rashes), aging, sun damage, environmental toxins, stress and poor diet, smoothing rough skin, reducing and/or eliminating warts and other skin imperfections, naturalizing skin color to its original condition (reducing discoloration) and treating damaged skin (including cracked skin), rashes from poison ivy, poison oak and other environmental insults, such as sun damage, environmental toxins stress and poor diet. In a particular embodiment of the present invention, an effective amount of at least one compound set forth above, optionally in combination with an additional bioactive agent such as an antiacne agent or a vitamin or other nutritional supplement (e.g., vitamin A, C, E, coenzyme Q, aloe vera, an antibiotic, among others) is administered to a patient in need to treat acne as the same composition is inhibiting and/or resolving acne scarring.

BRIEF DESCRIPTION OF DRAWINGS

FIG. 2 shows a number of the compounds according to the present invention and references for their synthesis.

FIGS. 3-5 show a number of compounds according to the present invention and their Nfr2 activation activity.

FIG. 6 shows a number of compounds according to the present invention and their NF-kB inhibition activity.

FIG. 7 shows the effect of the application of a composition according to the present invention on wrinkles of a subject after 45 days and 90 days of treatment.

FIG. 8 shows the treatment of the subject from FIG. 7 in mirrored image presentation for non-treated skin and skin treated for 45 days.

FIG. 9 shows the treatment of wrinkles in another subject after 14 days and 28 days of treatment.

FIG. 10 shows the treatment of acne scars after 45 and 90 days of treatment.

FIG. 11 shows the treatment of wrinkles in a male subject after 14 days of treatment.

FIG. 13 shows the effect of skin smoothing and beautification in a male subject after 49 days of treatment.

FIGS. 15-17 show that stretch marks were substantially reduced when treated with serum containing LD55 for 30 days.

FIGS. 19-20 show the effects on facial wrinkles in a subject treated with serum containing LD55 for 30 days.

FIG. 23 shows the effect on the overall rejuvenation of skin on the face of a subject who was treated with serum containing LD55 for 30 days.

DETAILED DESCRIPTION

Figure 1:
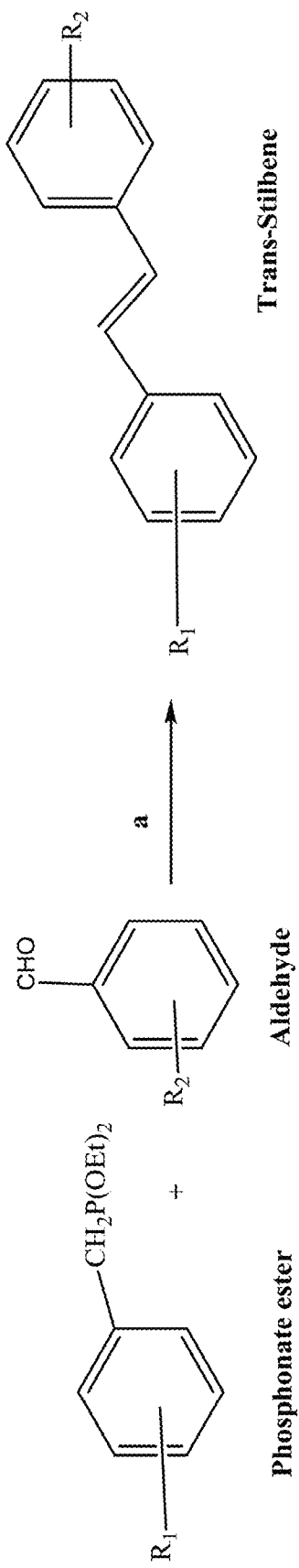
FIG. 1 shows scheme I, which is directed to the chemical synthesis of compounds according to the present invention. In scheme I, a substituted phosphonate ester is reacted with a substituted aldehyde under reaction conditions a to produce the substituted stilbene compound. The reaction conditions a employed are: (a) $R_1$ substituted phosphonate ester (1.5 equiv), NaH (2 equiv), dry THF, 0° C., 30 min, $R_2$ substituted aldehyde (1.0 equiv), 0° C. to rt, 20 h, then H2O/HCl; see FIG. 2, Table 1.

Unless otherwise specified, "a," "an," "the," and "at least one" are used interchangeably and mean one or more than one, depending on the context of use.

The following terms shall be used to describe the present invention. In instances where a term is not defined herein, such term is given its common meaning by those of ordinary skill in the art.

The term "patient" or "subject" refers to a mammal, preferably a human, including a domesticated mammal (including a dog, cat, sheep, horse, cow, pig, goat or other domesticated mammal in need of treatment or therapy to which compounds according to the present invention are administered in order to treat a condition or disease state otherwise described herein.

The term "compound", as used herein, unless otherwise indicated, refers to any specific chemical compound disclosed herein and includes within context, tautomers, regioisomers, geometric isomers, and where applicable, optical isomers thereof where applicable, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures)

as well as specific enantiomers or enantiomerically enriched mixtures of disclosed compounds. The compounds of this invention include all pharmaceutically acceptable salt forms, solvates, polymorphs and prodrug forms of the present compounds, where applicable. The present invention relates to both the cis- and trans-stilbene structures, preferably, trans structures as generally presented herein and their methods of use.

The term "effective amount" shall mean an amount of a composition or component which is included in a composition according to the present invention to effect an intended result, depending on the nature of the composition and/or component described.

The term "modulate" means, with respect to disease states or conditions, modulated through (e.g, by binding) or having an effect on NF-κB and/or Nrf2 signaling pathways to produce, either directly or indirectly, an improvement or lessening of a condition or disease state which was, prior to administration of a compound according to the present invention, sub-optimal and in many cases, debilitating. While not being limited by way of theory, it is believed that modulation occurs by virtue of antagonist/inhibitor activity for NF-κB and agonist activity for Nrf2 signalling pathway activity, among other activity. In most/many instances, the term modulate shall mean direct or indirect inhibition or enhancement/up-regulation of NF-κB/Nrf2 signalling pathways alone or within the context of treating a condition or providing a cosmetic improvement to hair, skin and nails as otherwise described herein.

In one exemplary embodiment, a compound for use in the present invention is LD-55 (see Table 2). The anti-inflammatory activity of LD55 works primarily through inhibition of NF-KappaB [2, second set of references]. The antioxidant activity works primarily through activation of NRF2 [3, second set of references]. Pursuant to the present invention, the inventors have combined the LD-55 molecule with carrier and essential oils that also have anti-inflammatory and anti-oxidant activity, however they work through different, but complementary pathways. The carrier oils also stimulate other pathways that enhance the activity of LD55. In addition, the carrier oils contain skin penetration enhancing terpenes which assist in the delivery of actives in compositions according to the present invention and provide an effective penetration of actives into the skin of a subject being treated with compositions according to the present invention. Preferred carrier oils are the essential oils such as lavender, *melaleuca*, peppermint, frankincense, *eucalyptus* and mixtures thereof each of which oils comprises a natural terpene which may function as a skin penetration agent. One or more terpenes may be included in compositions in penetration enhancing effective amounts to improve the activity of compositions according to the present invention. These terpenes include α-pinene, β-pinene, camphene, β-myrcene, δ-3-carene, α-terpinene, cis-ocimene, limonene, p-cymene, trans-ocimene, γ-terpinene, terpinolene, linalool, geraniol, β-caryophyllene, cis-nerolidol, trans-nerolidol and mixtures thereof, each of which may be included as separate individual components in compositions according to the present invention or as components in essential oils which may be included in compositions according to the present invention.

The term "independently" is used herein to indicate that the variable, which is independently applied, varies independently from application to application.

The term "cosmetic condition" is used to describe distressed states or conditions of the skin, hair and nails which are enhanced, treated, inhibited or resolved, by one or more compositions according to the present invention which include compounds as described herein which modulate NF-κB signaling pathways (via inhibition) and Nrf2 signaling pathways (by up regulation) such that compounds which both inhibit NF-κB signaling and increase Nrf2 signaling may be used to treat these distressed states and/or conditions. These distressed states and/or conditions include for example, wrinkles and cellulite, acne scars, other scars that won't heal or are hard to heal, stretch marks, rashes, repairing damaged skin, smoothing rough skin, reducing and/or eliminating warts and other skin imperfections, naturalizing skin color to its original condition and treating damaged skin and rashes from poison ivy and poison oak and other environmental insults. Compositions for use in the present invention are particularly useful for rejuvenating and beautifying keratinous tissue, especially skin tissue (enhancing the appearance and/or feel of the skin).

The term "coadministration" or "combination therapy" is used to describe a therapy in which at least two active compounds in effective amounts are used to treat a disease state or condition as otherwise described herein at the same time. This term includes the administration of an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, antibiotics (e.g. tetracyclines including doxycycline, limecycline and minocycline; clindamycin, erythromycin, trimethoprime and cotrimoxazole, among others), pharmaceutically acceptable salts and esters thereof and the like and mixtures thereof, among others), vitamin C, vitamin E, vitamin A, coenzyme Q, aloe vera, and other agents which are useful to enhance the appearance of skin along with cosmetic compositions according to the present invention. Co-administration can occur by the additional agent being incorporated into the cosmetic composition or simply being co-administered along with the composition. Although the term coadministration preferably includes the administration of two active compounds to the patient at the same time, it is not necessary that the compounds be administered to the patient at the same time, although effective amounts of the individual compounds will be present in the patient at the same time to effect an intended result. In certain aspects of the invention, one or more compounds according to the present invention may be administered with, for example, an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, antibiotics (e.g. tetracyclines including doxycycline, limecycline and minocycline; clindamycin, erythromycin, trimethoprime and cotrimoxazole, among others) pharmaceutically acceptable salts and esters thereof and the like and mixtures thereof, among others), vitamin C, vitamin E, vitamin A, coenzyme Q, aloe vera and other agents which are useful to enhance the appearance of skin along with cosmetic compositions according to the present invention. Coadministration of one of the present compounds with another agent as otherwise described herein will often result in a synergistic enhancement of the activity of the other agent, an unexpected result.

"Treat", "treating", and "treatment", etc., as used herein, refer to any action providing a benefit to a patient at risk for or afflicted with a skin condition as otherwise described herein, including improvement in the condition through lessening or suppression of at least one symptom, delay in progression of the condition, resolution and/or inhibition of the condition.

"Pharmaceutically acceptable" or "cosmetically acceptable" as used herein means that the compound or composition is suitable for administration, preferably topical application to a subject to achieve the treatments and/or benefits described herein, without unduly deleterious side effects in light of the severity of the conditions and necessity of the treatment. It is noted that the compositions described herein may also be formulated for administration by routes other than topical.

"Inhibit" as used herein refers to the partial or complete elimination of a potential effect, while inhibitors are compounds that have the ability to inhibit. "Resolve" as used herein refers to the substantial resolution, including a complete resolution of a condition to be treated.

The present invention includes the compositions comprising the pharmaceutically acceptable salt. i.e., the acid or base addition salts of compounds of the present invention and their derivatives, where applicable. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

The term "rejuvenate" is used to describe damaged keratinous tissue, especially skin tissue which has been improved to a more normal, natural state, including the appearance and feel of the tissue, especially including the elasticity, softness and moisturizing qualities of the tissue. The term "beautify" refers to taking skin and enhancing its appearance and feel.

The term "additional agent" is used to describe an additional compound which may be coadministered with one or more compounds in cosmetic compositions of the present invention in the treatment of skin, especially acne. Such agents include, for example, antiacne agents (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, antibiotics (e.g. tetracyclines including doxycycline, limecycline and minocycline; clindamycin, erythromycin, trimethoprime and cotrimoxazole, among others), pharmaceutically acceptable salts and esters thereof and the like and mixtures thereof, among others), and other agents such as vitamin C, vitamin E, vitamin A, coenzyme Q, aloe vera and other agents which are useful to enhance the appearance of skin. Additional agents also include one or more terpenes (which may be included in essential oils which are incorporated into compositions according to the present invention) such as α-pinene, β-pinene, camphene, β-myrcene, δ-3-carene, α-terpinene, cis-ocimene, limonene, p-cymene, trans-ocimene, γ-terpinene, terpinolene, linalool, geraniol, β-caryophyllene, cis-nerolidol, trans-nerolidol and mixtures thereof.

Because of the dual activity exhibited by compounds according to the present invention, it has been discovered that these compounds may be used to effectively treat numerous disease states or conditions of keratinous tissue in patients or subjects who suffer from those conditions or disease states or are at risk for those conditions. In this method, at least one of these dual activity compounds, alone or in further combination with at least one additional bioactive agent in an effective amount is administered to a patient in need of to treat or reduce the likelihood of the occurrence or worsening of the condition(s) or state(s) of the keratinous tissue. The compounds and methods of the invention are useful for treating, resolving, inhibiting and/or reducing the likelihood or worsening of any the following skin conditions. These disease states and/or conditions include for example, wrinkles and cellulite, acne scars, other scars that won't heal, stretch marks, rashes, repairing damaged skin (including cracked skin), smoothing rough skin, reducing and/or eliminating warts and other skin imperfections, naturalizing skin color to its original condition and treating damaged skin and rashes from poison ivy and poison oak and other environmental insults. The compositions may be used generally to beautify and rejuvenate skin.

Compositions according to the present invention may be administered by any conventional means known in the art, preferably by simply applying a cosmetic composition topically to the skin, hair or nails of a subject in need. Pharmaceutical formulations include those suitable for oral, rectal, nasal, topical (including buccal and sub-lingual), vaginal or parenteral (including intramuscular, sub-cutaneous and intravenous) administration, but compositions which are administered by topical and/or transdermal route of administration directly at the site in the skin of the disease state or condition to be treated are clearly preferred. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

Cosmetic topical compositions for use in the present invention comprise at least one compound as described herein, optionally in combination with an additional active agent (such as an antiacne or other agent as described herein), further in combination with at least one additional cosmetic additive selected from a solvent (e.g. alcohol or other water compatible cosmetically acceptable solvent), a water incompatible solvent, emollients, humectants, oils (polar and non-polar which may provide oil-in-water or water-in-oil emulsions), conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, preservatives and mixtures thereof, among others. Compositions according to the present invention also optionally include an additional bioactive agent, such as an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), vitamin C, vitamin E, vitamin A, coenzyme Q, aloe vera and other agents which are useful to enhance the appearance of skin. In certain embodiments, cosmetic compositions comprise at least two of the above-described compounds, preferably LD-55 in combination with an essential oil or terpene as described above.

In embodiments, a combination of effective amounts of LD-55 and coconut oil and/or jojoba oil is preferred, and this mixture is combined with at least one additional cosmetic additive selected from a solvent (e.g. alcohol or other water compatible cosmetically acceptable solvent), a water incompatible solvent, emollients, humectants, oils (other than the above oils, such as polar and non-polar which may provide oil-in-water or water-in-oil emulsions), conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, preservatives and mixtures thereof, among others. Compositions according to the present invention also optionally include an additional bioactive agent, such as an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), vitamin C, vitamin E, vitamin A, coenzyme Q, aloe vera and other agents which are useful to enhance the appearance of skin. Penetration enhancing terpenes such as such as α-pinene, β-pinene, camphene, β-myrcene, δ-3-carene, α-terpinene, cis-ocimene, limonene, p-cymene, trans-ocimene, γ-terpinene, terpinolene, linalool, geraniol, β-caryophyllene, cis-nerolidol, trans-nerolidol and mixtures thereof may also be separately added in effective amounts to the compositions to enhance activity and performance.

The anti-oxidant activity of the stilbenes and dienone compounds (LD-55 is preferred) work primarily through activation of NRF2 [reference 3, second reference set] and the present invention preferably combines these molecules (especially LD-55) with carrier and essential oils that also have anti-inflammatory and anti-oxidant activity, but which work through different, but complementary pathways. The carrier oils also stimulate other pathways that enhance the activity of the stilbenes and dienone compounds (especially LD55).

For example, Jojoba Oil, a preferred oil used in the present invention, increases the wound healing process by activation of PI3K-Akt-mTOR pathway, and of the p38 and ERK1/2 MAPks. This oil also stimulates fibrobalsts to produce more collagen 1, but does not increase MMPs [reference 4, second set of references]. It has been shown that chronic inflammation inhibits wound healing [references 5, 6, second set of references]. Therefore, a strong anti-inflammatory agent, such as LD55 or other stilbene or dienone as described herein, enhances the wound healing properties of Jojoba oil through inhibition of chronic inflammation.

Coconut oil is also a preferred oil for inclusion in compositions according to the present invention alone or in combination with other oils, especially including jojoba oil. Coconut oil has been shown to increase the healing of skin. Studies have shown that coconut oil increase collagen production and higher levels of collagen cross linking. It also increase anti-oxidants such as glutathione [reference 7, second set of references]. Because LD55 anti-oxidant activity works through activation of the transcription factor NRF2, the mechanisms of LD55 and coconut oil are believed to work synergistically.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous, intramuscular or intraperitoneal dosage form, as well as via other parenteral routes, such as transdermal, buccal, subcutaneous, suppository or other route, including via inhalation or intranasally. Topical routes of administration are preferred, but these tend to be formulated as cosmetic compositions. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Cosmetic compositions for topical administration include ointments, powders and sprays. In addition to active compounds, cosmetic compositions include for example, at least one additional cosmetic additive selected from a solvent (e.g. alcohol or other water compatible cosmetically acceptable solvent), a water incompatible solvent, emollients, humectants, oils (polar and non-polar which may provide oil-in-water or water-in-oil emulsions), conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, preservatives and mixtures thereof, among others.

Generally, dosages and routes of administration of the pharmaceutical compositions and therapeutic compounds described herein are determined according to the size and condition of the subject, according to standard practice. Dose levels employed can vary widely, and can readily be determined by those of skill in the art. Typically, amounts in the milligram up to gram quantities are employed, depending the area affected, the severity of the disease and the age of the subject.

The dosage administered pursuant to the present invention is an effective amount for producing an intended result and will vary depending upon known factors such as the penetration kinetics and/or pharmacodynamic characteristics of the particular agent and the ability of the agent to penetrate the tissue to which the composition has been administered or applied, as well as the age, health, and weight of the recipient; nature and extent of symptoms, kind of concurrent treatment, frequency of treatment, and the effect desired. Usually a daily dosage of active compound can be about 0.01 to 500 milligrams per kilogram of body weight or more, often 0.1 milligrams to 250 milligrams per kilogram of body weight. Ordinarily, 0.5 to 50, and often 1 to 25 milligrams per kilogram per day given in divided doses 1 to 6 times a day or in sustained release form (often, transdermal administration) is effective to obtain desired results.

The active compounds may be used at a concentration of 0.01 to 99.9 weight percent of the formulation, or in some cases a concentration of 0.001 to 99.9 weight percent of the formulation. Often the active compound is included the composition in amounts ranging from 0.01 wt % to up to 10 wt % or more, often 0.1 wt % to about 5 wt %. Cosmetic compositions for application directly to the skin are preferably formulated in lotions, creams, salves or liquids. Many of these compositions comprise water-in-oil or oil-in-water emulsions with the active compounds being included therein. The topical formulation dosage with vary with the amount applied to the area of tissue to be treated. In contrast, the pharmaceutical formulation, when used, is preferably in unit dosage form. The unit dosage form can be a capsule or tablet itself, or the appropriate number of any of these. The quantity of active compound in a unit dose of composition may be varied or adjusted from about 0.05 to several grams, often 0.1 to about 1000 milligrams or more or about 1 milligram to 500 milligrams according to the particular treatment involved. Compositions (dosage forms) suitable for internal administration contain from about 1 milligram to about 1000 milligrams of active compound per unit. In these pharmaceutical compositions the active compound will ordinarily be present in an amount of about 0.5-95% by weight based on the total weight of the composition.

Exemplary Cosmetic Compositions According to the Present Invention

The present invention may be formulated as cosmetic compositions as follows:
1. As a face cleanser or toner composition;
2. As a facial lotion for rejuvenating and/or beautifying the face
3. As a body lotion or wash for rejuvenating and/or beautifying skin
4. As a lotions, solution, cream or salve for resolving skin imperfections, smoothing skin and treating acne scars and other scars, including hard to resolve scars and stretch marks
5. As a shampoo for enhancing or rejuvenating hair, including enhancing the luster and repair of damaged hair
6. As a moisturizing composition for treating rough and damaged skin
7. As a cream or polish for treating nails to repair damaged and cracked nail/ungula tissue and resolve discoloration
8. As an after shave lotion
9. As a cream for treating acne and acne scars and otherwise smoothing bumps and irregularities in skin
10. As a cream for treating wrinkles and toning skin, alone or in combination with one or more vitamins or supplements (e.g. vitamin A, C, E, coenzyme Q, aloe vera)
11. As a lotion for the treatment of environmental toxins and the rashes that result, including poison oak, poison ivy
12. As a hand lotion or hand cream, which may include surfactants for cleansing the hands
13. As a hand sanitizer
14. As a cream or lotion for treating warts, removing skin tags and smoothing skin irregularities Treatment Using the Present Compounds Treatment, as defined herein, is the amelioration of the symptoms associated with disease. Symptoms may be reduced either by decreasing the level of the condition itself, or by decreasing the symptoms associated with the condition. In most instances, favorable treatment results in keratinous tissue being favorable enhanced by enhancing or beautifying skin or resolving and/or favorably influencing the tissue condition for which the composition is applied. The subject of the treatment is preferably a mammal, such as a domesticated farm animal (e.g., cow, horse, pig, or a domesticated pet (e.g., dog, cat). More preferably, the subject is a human.

As noted herein, and without being bound by any particular theory, one mechanism by which administration of the compounds according to the present invention may treat skin conditions is through inhibition of the activity of NF-κB and up-regulation (increasing) the activity of Nrf2. Inhibition of NF-κB results in a decrease in NF-κB activity, and includes direct inhibition and indirect inhibition. Direct inhibition is the direct effect of a compound on NF-κB and its activity. For example, one type of direct inhibition of NF-κB is a block of NF-κB DNA interactions. Indirect inhibition, on the other hand, involves the effect of a compound involved in the regulation of NF-κB that leads to a decrease in NF-κB activity. For example, as phosphorylation of the NF-κB regulator IκB by IκB kinases (IKK) or Src family kinases (SFK) results in a dysregulation of NF-κB, and an according increase in NF-κB activity, inhibition of IKK or SFK by the present compounds provides an example of indirect inhibition.

Increase in Nrf2 results in an increase or up-regulation of Nfr2 activity, and includes direct agonist activity and indirect agonist activity. Direct enhancement is the direct effect of a compound on Nrf2 (or its subunits) and its activity. Indirect inhibition, on the other hand, involves the effect of a compound according to the present invention in the regulation of Nrf2 that leads to an increase in Nrf2 activity. It was unexpected that the compositions according to the present invention could so favorably enhance skin from a cosmetic perspective and otherwise treat and/or resolve conditions of keratinous tissue which were not known to be modulated and/or related to NF-κB and/or Nrf2 activity.

EXAMPLES

Chemical Synthesis

The synthesis of 56 substituted trans (E)-stilbenes was accomplished using Homer-Wadsworth-Emmons (HWE) olefination chemistry[24], and as otherwise described in the art[25,21] (see also, Deck, et al., *Bioorg Med Chem.* 2017 Feb. 15; 25(4):1423-1430) and in detail hereinbelow. HWE chemistry was used to avoid formation of a mixture of E and Z isomers and formation of triphenylphosphine oxide, which complicates the purification process.

In the case of enone compounds according to the present invention, these are synthesized by methods which are well-known in the art and which are alternatively presented in Deck, et al., *Eur J Med Chem.* 2018 Jan. 1; 143:854-865, which is incorporated by reference herein.

Reporter Assays:

A Nrf2-ARE reporter-HepG2 stable cell line (BPS Bioscience, San Diego, CA) is grown in a humidified atmosphere at 37° C. in 5% $CO_2$/95% air. The cells are maintained in MEM medium with Earles balanced salts and L-glutamine supplemented with 10% fetal bovine serum (FBS), 1 mM sodium pyruvate, 1% non-essential amino acids, 100 units/ml penicillin, 100 µg/ml streptomycin, and 400 µg/ml Geneticin. One day prior to treatment, the Nrf2-ARE cells are plated into 24-well cell culture plates at approximately 30% confluency in the above media without Geneticin. The following day, fresh media with or without substituted trans stilbene or sulforaphane is applied to the cells. DMSO concentrations are kept at 0.1%. The cells are again placed in a humidified atmosphere at 37° C. in 5% $CO_2$/95% air for 5 hours. Plate wells are gently washed with phosphate buffered saline (PBS) pH 7.4 and lysed with 1× passive lysis buffer (Promega, Madison, WI, USA). The subsequent lysates are analyzed with the Luciferase Assay System (Promega) utilizing a GloMax 20/20 luminometer (Promega, Sunnyvale, CA, USA). The firefly luciferase relative light units are normalized to protein (mg/ml) with BCATM Protein Assay Kit protein (Pierce, Rockford, IL, USA)

An NFkB reporter stable cell line from human 293Tembryonic kidney cells (293T/NFkB-luc) (Panomics, Inc., Redwood City, CA) was grown in a humidified atmosphere at 37° C. in 5% $CO_2$/95% air. The cells were maintained in Dulbecco's modified Eagle's medium (DMEM—high glucose containing 4 mM glutamine) supplemented with 10% fetal bovine serum (FBS), 1 mM sodium pyruvate, 100 U/ml penicillin, 100 ug/ml streptomycin, and 100 ug/ml hygromycin (Gibco/Invitrogen, Carlsbad, CA) to maintain cell selection. One day prior to treatment, the 293T/NFkB-luc cells were plated into 24-well cell culture plates (Costar, Cambridge, MA) at approximately 70% confluency in the above media without hygromycin. The following day cells were fed fresh media 1 h prior to treatment. Media with or without recombinant tumor necrosis factor alpha (TNFa) (R&D Biosciences/Clontech, Palo Alto, CA) were then applied to the cells at 20 ng/ml followed by immediate treatments with inhibitor. The cells were placed again in a humidified atmosphere at 37° C. in 5% $CO_2$/95% air for 7 h. Plate wells were gently washed with phosphate-buffered saline, pH 7.4, and lysed with 1× passive lysis buffer (Promega, Madison, WI). The subsequent lysates were analyzed with the Luciferase Assay System (Promega) utilizing a TD-20/20 luminometer (Turner Designs, Sunnyvale, CA). The firefly luciferase relative light units were normalized to protein (mg/ml) with BCATM Protein Assay Kit (Pierce, Rockford, IL) and standardized to percent of control (TNFa control). For assays of cell viability, cells were treated similarly as above and with 15 uM inhibitor. After washing, cells were treated with 100 ul media and 20 ul CellTiter 96 AQueous One Solution reagent for 1 h and then read at 490 nm with a Spectromax plate reader.

Synthesis

Reagents were purchased from commercial sources (Aldrich, Acros, etc.). Tetrahydrofuran was distilled from lithium aluminum hydride. Thin layer chromatography was carried out on silica gel 60F254 plates. All compounds were shown to be >98% pure by $^1$H NMR and/or $^{13}$C NMR unless otherwise noted. Column chromatographic separations were performed by using EM type 60 silica gel (230-400 mesh). Melting points were taken on a Thomas-Hoover Uni-Melt capillary melting point apparatus and reported uncorrected. Unless otherwise noted, $^1$H spectra were recorded by using $CDCl_3$ solutions at 300 MHz; $^{13}$C NMR spectra were recorded in $CDCl_3$ at 75 MHz; $^{19}$F were recorded in $CDCl_3$ at 282 MHz. Chemical shifts are reported in ppm relative to $CDCl_3$ at 7.24 ppm for $^1$H NMR and 77.0 ppm for $^{13}$C NMR and the external standard hexafluorobenzene for $^{19}$F NMR at −164.9 ppm. Peak assignments were made with the aid of DEPT spectra. $^1$H NMR data are reported as follows: chemical shift, multiplicity (s=singlet, d=doublet, t=triplet, q=quartet, dd=doublet of doublets, td=triplet of doublets, m=multiplet), coupling constant (J in Hz) and integration. High resolution mass spectra (HRMS) were obtained at the UNM Mass Spectrometry Facility, Albuquerque, New Mexico General Procedure for Synthesis of Phosphonate Esters Benzyl chloride or benzyl bromide derivatives (1 eq) were added to triethylphosphite (1.5 eq) and heated to 130° C. for 20 h. After cooling, the resulting crude product was distilled in vacuo to remove excess triethylphosphite and ethyl chloride or ethyl bromide. Purification by filtration through a pad of silica gel (70% ethyl acetate/30% hexanes) gave the phosphonate ester products as colorless oils.

General Procedure for Synthesis of Stilbenes

The appropriately substituted phosphonate ester (10 mmol) was dissolved in dry tetrahydrofuran (20 ml) and stirred at 0-5° C. Sodium hydride (25 mmol) was added to the solution slowly and after thirty minutes the appropriate freshly distilled aldehyde (10 mmol) in tetrahydrofuran (30 ml) was added dropwise. The mixture was allowed to stir at room temperature overnight. In order to increase the yield, compounds 35, 37 and 40 were heated under reflux for 3-4 hours. The mixture was cooled and quenched with ice water (10 ml) and poured onto ice. Dilute hydrochloric acid (1M) was added until acidic and the solution was extracted with ethyl acetate (4×50 ml). The combined organic layers were washed with saturated salt and dried over magnesium sulfate. Filtration and evaporation of the ethyl acetate afforded crude stilbene products as oils or solids. The solids were crystallized from 95% ethanol to afford crystalline stilbenes. The oils were chromatographed on silica gel using methylene chloride to give pure products.

(E)-1-Fluoro-2-(2-methoxystyryl)benzene 10: 98% yield, white crystals; mp 34-35° C.; $^1$H NMR ($CDCl_3$, 300 MHz): δ7.66 (dt, J=7.8, 1.6 Hz, 1H), 7.62 (dd, J=7.6, 1.5 Hz, 1H), 7.54 (d, J=16.6 Hz, 1H), 7.27 (d, J=16.6 Hz, 1H), 7.22 (m, 2H), 7.13 (dt, J=7.5, 1.3 Hz, 1H), 7.05 (dt, J=8.0, 1.3 Hz, 1H), 6.98 (t, J=7.4 Hz, 1H), 6.91 (d, J=8.3 Hz, 1H), 3.88 (s, 3H). $^{13}$C NMR ($CDCl_3$, 75 MHz): δ 160.5 (d, J=247.7 Hz), 157.2 (s), 129.2 (s), 128.6 (d, J=8.4 Hz), 127.0 (d, J=3.4 Hz), 126.7 (s), 126.5 (s), 126.0 (d, J=12.1 Hz), 125.7 (d, J=3.6 Hz), 124.2 (d, J=3.1 Hz), 121.1 (d, J=4.0 Hz), 120.9 (s), 115.5 (d, J=22.2 Hz), 110.8 (s), 55.7 (s). $^{19}$F ($CDCl_3$, 282

MHz): δ–116.9 (s, 1F). HRMS (EI) calcd for $C_{15}H_{13}FO$ [M]$^+$: 228.0950; found, 228.0950.

(E)-1-(3-Fluorostyryl)-2,3-dimethoxybenzene 16: 98% yield, oil; $^1$H NMR (CDCl$_3$, 300 MHz):
δ 7.45 (d, J=16.5 Hz, 1H), 7.27 (m, 3H), 7.23 (dd, J=7.9, 1.3 Hz, 1H), 7.08 (d, J=16.5 Hz, 1H), 7.06 (t, J=8.1 Hz, 1H), 6.96 (m, 1H), 6.86 (dd, J=8.1, 1.4 Hz, 1H), 3.88 (s, 3H), 3.87 (s, 3H). $^{13}$C NMR (CDCl$_3$, 75 MHz): δ 163.2 (d, J=245.1 Hz), 153.3 (s), 147.3 (s), 140.1 (d, J=7.6 Hz), 131.0 (s), 130.1 (d, J=8.4 Hz), 128.7 (s), 124.3 (s), 124.2 (s), 122.6 (s), 117.9 (s), 114.4 (d, J=21.5 Hz), 112.9 (d, J=21.8 Hz), 111.8 (s), 61.2 (s), 56.0 (s). $^{19}$F (CDCl$_3$, 282 MHz): δ–111.9 (s, 1F). HRMS (EI) calcd for $C_{16}H_{15}FO_2$ [M]$^+$: 258.1056; found, 258.1058.

(E)-1-(4-Fluorostyryl)-2,3-dimethoxybenzene 17: 87% yield, white crystals; mp 50-51° C.; $^1$H NMR (CDCl$_3$, 300 MHz): δ 7.50 (dd, J=8.4, 5.6 Hz, 2H), 7.36 (d, J=16.5 Hz, 1H), 7.21 (d, J=7.8 Hz, 1H), 7.07 (d, J=16.4 Hz, 1H), 7.04 (m, 3H), 6.83 (d, J=7.6 Hz, 1H), 3.87 (s, 3H), 3.85 (s, 3H). $^{13}$C NMR (CDCl$_3$, 75 MHz): δ 162.4 (d, J=247.1 Hz), 153.2 (s), 147.0 (s), 133.9 (d, 2.9 Hz), 131.4 (s), 128.7 (s), 128.2 (d, J=7.9 Hz), 124.2 (s), 122.8 (s), 117.8 (s), 115.6 (d, J=21.6 Hz), 111.5 (s), 61.1 (s), 55.8 (s). $^{19}$F (CDCl$_3$, 282 MHz): δ–112.7 (s, 1F). HRMS (EI) calcd for $C_{16}H_{15}FO_2$ [M]$^+$: 258.1056; found, 258.1060.

(E)-2-(4-Fluorostyryl)-1,4-dimethoxybenzene 18: 74% yield, white crystals; mp 58-59° C.; $^1$H NMR (CDCl$_3$, 300 MHz): δ 7.49 (dd, J=8.7, 5.5 Hz, 2H), 7.37 (d, J=16.4 Hz, 1H), 7.13 (d, J=2.6 Hz, 1H), 7.05 (d, J=16.4 Hz, 1H), 7.03 (t, J=8.7 Hz, 2H), 6.80 (m, 2H), 3.83 (s, 3H), 3.81 (s, 3H). $^{13}$C NMR (CDCl$_3$, 75 MHz): δ 162.3 (d, J=247.0 Hz), 153.8 (s), 151.4 (s), 134.0 (d, 3.1 Hz), 128.1 (s), 128.0 (d, J=7.7 Hz), 123.1 (s), 115.6 (d, J=21.6 Hz), 113.7 (s), 112.2 (s), 111.7 (s), 56.2 (s), 55.7 (s). $^{19}$F (CDCl$_3$, 282 MHz): δ–112.9 (s, 1F). HRMS (EI) calcd for $C_{16}H_{15}FO_2$ [M]$^+$: 258.1056; found, 258.1057.

(E)-1,2-Difluoro-4-(4-methylstyryl)benzene 22: 97% yield, white crystals; mp 90-92° C.; $^1$H NMR (CDCl$_3$, 300 MHz): δ 7.38 (d, J=8.1 Hz, 2H), 7.29 (m, 1H), 7.16 (d, J=8.1 Hz, 2H), 7.13 (m, 2H), 6.99 (d, J=16.4 Hz, 1H), 6.92 (d, J=16.4 Hz, 1H), 2.36 (s, 3H). $^{13}$C NMR (CDCl$_3$, 75 MHz): δ 151.7 (dd, J=69.7, 13.3 Hz), 148.5 (dd, J=70.7, 13.3 Hz), 138.0 (s), 134.9 (t, J=5.0 Hz), 133.9 (s), 129.7 (s), 129.5 (s), 126.5 (s), 125.5 (s), 122.6 (dd, J=6.1, 2.9 Hz), 117.3 (d, J=17.5 Hz), 114.5 (d, J=17.6 Hz), 21.3 (s). $^{19}$F (CDCl$_3$, 282 MHz): δ–136.3 (d, J=20.9 Hz, 1F), –137.7 (d, J=20.9 Hz, 1F). HRMS (EI) calcd for $C_{15}H_{12}F_2$ [M]$^+$: 230.0907; found, 230.0911.

(E)-1,4-Difluoro-2-(4-methoxystyryl)benzene 23: 60% yield, pale yellow crystals; mp 109-110° C.; $^1$H NMR (CDCl$_3$, 300 MHz): δ 7.46 (d, J=8.6 Hz, 2H), 7.25 (m, 1H), 7.06 (s, 2H), 6.98 (m, 1H), 6.89 (d, J=8.6 Hz, 2H), 6.86 (m, 1H), 3.81 (s, 3H). $^{13}$C NMR (CDCl$_3$, 75 MHz): δ 159.8 (s), 159.2 (d, J=200.2 Hz), 156.0 (d, J=201.6 Hz), 131.5 (d, J=3.9 Hz), 129.5 (s), 128.1 (s), 127.0 (dd, J=14.5, 8.2 Hz), 117.6 (s), 116.7 (dd, J=25.4, 8.7 Hz), 114.5 (dd, J=24.5, 9.0 Hz), 114.2 (s), 112.4 (dd, J=24.6, 3.8 Hz), 55.3 (s). $^{19}$F (CDCl$_3$, 282 MHz): δ–117.7 (d, J=17.2 Hz, 1F), –122.9 (d, J=17.2 Hz, 1F). HRMS (EI) calcd for $C_{15}H_{12}F_2O$ [M]$^+$: 246.0856; found, 246.0852.

(E)-1,2-Difluoro-4-(2-fluorostyryl)benzene 24: 82% yield, white crystals; mp 85-86° C.; $^1$H NMR (CDCl$_3$, 300 MHz): δ 7.56 (dt, J=7.7, 1.6 Hz, 1H), 7.33 (dt, J=7.7, 1.8 Hz, 1H), 7.23 (m, 1H), 7.17 (d, J=16.4 Hz, 1H), 7.10 (m, 3H), 7.05 (d, J=16.3 Hz, 1H). $^{13}$C NMR (CDCl$_3$, 75 MHz): δ 160.7 (d, J=247.9 Hz), 152.1 (dd, J=44.2, 12.0 Hz), 148.8 (dd, J=46.6, 12.0 Hz), 134.7 (t, J=6.2 Hz), 129.4 (d, J=8.4 Hz), 128.9 (s), 127.3 (d, J=3.2 Hz), 124.7 (d, J=11.9 Hz), 124.4 (d, J=2.7 Hz), 123.1 (dd, J=5.3, 3.0 Hz), 122.3 (s), 117.6 (d, J=17.5 Hz), 116.1 (d, J=22.1 Hz), 115.0 (d, J=17.6 Hz). $^{19}$F (CDCl$_3$, 282 MHz): δ–116.0 (s, 1F), –136.0 (d, J=20.8 Hz, 1F), –136.8 (d, J=21.1 Hz, 1F). HRMS (EI) calcd for $C_{14}H_9F_3$ [M]$^+$: 234.0656; found, 234.0652.

(E)-1,2-Difluoro-4-(4-methoxystyryl)benzene 26: 66% yield, white crystals; mp 73-74° C.; $^1$H NMR (CDCl$_3$, 300 MHz): δ 7.41 (d, J=8.6 Hz, 2H), 7.27 (m, 1H), 7.11 (m, 2H), 6.94 (d, J=16.5 Hz, 1H), 6.88 (d, J=8.7 Hz, 2H), 6.83 (d, J=16.5 Hz, 1H), 3.81 (s, 3H). $^{13}$C NMR (CDCl$_3$, 75 MHz): δ 159.8 (s), 151.8 (dd, J=79.6, 12.7 Hz), 148.6 (dd, J=81.0, 13.2 Hz), 135.2 (t, J=4.9 Hz), 129.6 (d, J=13.0 Hz), 129.5 (s), 128.0 (s), 124.5 (s), 122.5 (dd, J=5.4, 2.8 Hz), 117.5 (d, J=17.4 Hz), 114.5 (d, J=16.0 Hz), 114.4 (s), 55.5 (s). $^{19}$F (CDCl$_3$, 282 MHz): δ–136.4 (d, J=20.9 Hz, 1F), –138.1 (d, J=20.8 Hz, 1F). HRMS (EI) calcd for $C_{15}H_{12}F_2O$ [M]$^+$: 246.0856; found, 246.0860.

(E)-1,4-Difluoro-2-(2-fluorostyryl)benzene 29: 88% yield, white crystals; mp 79-81° C.; $^1$H NMR (CDCl$_3$, 300 MHz): δ 7.60 (dt, J=7.7, 1.6 Hz, 1H), 7.27 (s, 2H), 7.26 (m, 2H), 7.13 (dd, J=7.6, 1.1 Hz, 1H), 7.08 (m, 1H), 7.00 (m, 1H), 6.90 (m, 1H). $^{13}$C NMR (CDCl$_3$, 75 MHz): δ 160.6 (d, J=250.4 Hz), 159.3 (d, J=185.2 Hz), 156.1 (d, J=189.0 Hz), 129.6 (d, J=8.5 Hz), 127.2 (d, J=2.9 Hz), 126.5 (dd, J=14.4, 7.9 Hz), 124.6 (d, J=12.0 Hz), 124.3 (d, J=3.3 Hz), 124.1 (s), 122.0 (s), 116.8 (dd, J=25.3, 8.9 Hz), 115.9 (d, J=22.2 Hz), 115.5 (dd, J=24.5, 8.8 Hz), 112.8 (dd, J=24.7, 3.5). $^{19}$F (CDCl$_3$, 282 MHz): δ–115.9 (s, 1F), –117.3 (d, J=17.2 Hz, 1F), –122.4 (d, J=17.2 Hz, 1F). HRMS (EI) calcd for $C_{14}H_9F_3$ [M]$^+$: 234.0656; found, 234.0654.

(E)-1,2-Difluoro-4-(3-fluorostyryl)benzene 30: 95% yield, white crystals; mp 48-49° C.; $^1$H NMR (CDCl$_3$, 300 MHz): δ 7.30 (m, 2H), 7.16 (m, 4H), 6.98 (m, 1H), 6.96 (d, J=16.5 Hz, 1H), 6.90 (d, J=16.5 Hz, 1H). $^{13}$C NMR (CDCl$_3$, 75 MHz): δ 163.2 (d, J=245.6 Hz), 152.0 (dd, J=42.1, 11.1 Hz), 148.7 (dd, J=44.7, 11.1 Hz), 139.1, (d, J=7.8 Hz), 134.2 (t, J=5.9 Hz), 130.2 (d, J=8.4 Hz), 128.5 (s), 127.8 (s), 122.9 (dd, J=6.2, 3.6 Hz), 122.6 (d, J=2.3 Hz), 117.5 (d, J=17.5 Hz), 114.9 (d, J=5.3 Hz), 114.7 (s), 112.8 (d, J=21.9 Hz). $^{19}$F (CDCl$_3$, 282 MHz): δ–111.4 (s, 1F), –135.8 (d, J=20.9 Hz, 1F), –136.5 (d, J=20.8 Hz, 1F). HRMS (EI) calcd for $C_{14}H_9F_3$ [M]$^+$: 234.0656; found, 234.0660.

(E)-1,4-Difluoro-2-(3-fluorostyryl)benzene 34: 89% yield, white crystals; mp 73-74° C.; $^1$H NMR (CDCl$_3$, 300 MHz): δ 7.27 (m, 4H), 7.18 (d, J=16.5 Hz, 1H), 7.06 (d, J=16.6 Hz, 1H), 7.01 (m, 2H), 6.91 (m, 1H). $^{13}$C NMR (CDCl$_3$, 75 MHz): δ 163.2 (d, J=245.7 Hz), 159.3 (d, J=179.4 Hz), 156.0 (d, J=183.7 Hz), 139.0 (d, J=7.7 Hz), 130.8 (s), 130.2 (d, J=8.3 Hz), 126.1 (m), 122.8 (d, J=2.0 Hz), 121.2 (s), 116.9 (dd, J=25.3, 8.8 Hz), 115.5 (dd, J=24.5, 8.7 Hz), 115.1 (d, J=21.6 Hz), 113.1 (d, J=21.9 Hz), 112.8 (dd, J=24.6, 3.8 Hz). $^{19}$F (CDCl$_3$, 282 MHz): δ–111.5 (s, 1F), –117.3 (d, J=17.2 Hz, 1F), –122.0 (d, J=17.2 Hz, 1F). HRMS (EI) calcd for $C_{14}H_9F3$ [M]$^+$: 234.0656; found, 234.0659.

(E)-2,4-Difluoro-1-(3-fluorostyryl)benzene 35: 67% yield, white crystals; mp 60-61° C.; $^1$H NMR (CDCl$_3$, 300 MHz): δ 7.50 (dd, J=15.0, 8.3 Hz, 1H), 7.23 (m, 3H), 7.16 (d, J=16.5 Hz, 1H), 7.04 (d, J=16.5 Hz, 1H), 6.88 (m, 3H). $^{13}$C NMR (CDCl$_3$, 75 MHz): δ 163.2 (d, J=245.5 Hz), 163.1 (dd, J=143.9, 12.3 Hz), 159.8 (dd, J=146.1, 12.2), 139.5 (d, J=7.6 Hz), 130.2 (d, J=8.4 Hz), 129.4 (s), 128.0 (dd, J=9.4, 5.0 Hz), 122.5 (d, J=2.2 Hz), 121.3 (s), 121.1 (d, J=3.5 Hz), 114.8 (d, J=21.4 Hz), 112.9 (d, J=21.9 Hz), 11.7 (dd, J=22.0, 3.7 Hz), 104.2 (t, J=25.8 Hz). $^{19}$F (CDCl$_3$, 282 MHz):

δ−108.6 (d, J=6.1 Hz, 1F), −111.6 (s, 1F), −111.7 (d, J=6.3 Hz, 1F). HRMS (EI) calcd for $C_{14}H_9F_3$ [M]$^+$: 234.0656; found, 234.0658.

(E)-2,4-Difluoro-1-(2-fluorostyryl)benzene 36: 70% yield, white crystals; mp 84-85° C.; $^1$H NMR (CDCl$_3$, 300 MHz): δ 7.60 (t, J=8.8 Hz, 1H), 7.58 (t, J=8.7 Hz, 1H), 7.25 (s, 2H), 7.22 (m, 1H), 7.13 (dt, J=7.6, 1.3 Hz, 1H), 7.06 (dt, J=9.5, 1.3 Hz, 1H), 6.83 (m, 2H). $^{13}$C NMR (CDCl$_3$, 75 MHz): δ 162.6 (dd, J=250.5, 13.9 Hz), 162.3 (t, J=5.1 Hz), 158.9 (t, J=10.2 Hz), 129.3 (d, J=8.4 Hz), 128.1 (dd, J=9.5, 5.2 Hz), 127.2 (d, J=3.1 Hz), 125.1 (d, J=11.9 Hz), 124.4 (d, J=3.2 Hz), 122.9 (s) 122.2 (s), 121.7 (dd, J=11.7, 3.6 Hz), 116.0 (d, J=22.2 Hz), 111.8 (dd, J=21.6, 3.5 Hz), 104.3 (t, J=25.7 Hz). $^{19}$F (CDCl$_3$, 282 MHz): δ−108.8 (s, 1F), −112.2 (d, J=5.6 Hz, 1F), −116.4 (s, 1F). HRMS (EI) calcd for $C_{14}H_9F_3$ [M]: 234.0656; found, 234.0658.

(E)-2,4-Difluoro-1-(4-methylstyryl)benzene 37: 32% yield, white crystals; mp 72-73° C.; $^1$H NMR (CDCl$_3$, 300 MHz): δ 7.55 (dd, J=15.0, 8.4 Hz, 1H), 7.89 (d, J=7.9 Hz, 2H), 7.47 (d, J=7.5 Hz, 2H), 7.16 (d, J=16.5 Hz, 1H), 7.07 (d, J=16.5 Hz, 1H), 6.85 (m, 2H), 2.35 (s, 3H). $^{13}$C NMR (CDCl$_3$, 75 MHz): δ 162.9 (dd, J=131.0, 12.1 Hz), 159.5 (dd, J=133.5, 12.0 Hz), 137.9 (s), 134.3 (s), 130.5 (s), 129.5 (s), 127.7 (dd, J=9.2, 5.4 Hz), 126.5 (s), 121.8 (dd, J=12.5, 3.8 Hz), 118.9 (s), 111.5 (dd, J=21.5, 2.8 Hz), 104.1 (t, J=25.7 Hz), 21.4 (s). $^{19}$F (CDCl$_3$, 282 MHz): δ−109.7 (d, J=5.3 Hz, 1F), −112.4 (d, J=4.4 Hz, 1F). HRMS (EI) calcd for $C_{15}H_{12}F_2$ [M]$^+$: 230.0907; found, 230.0912.

(E)-1,4-Difluoro-2-(4-fluorostyryl)benzene 40: 50% yield, buff crystals; mp 76-77° C.; $^1$H NMR (CDCl$_3$, 300 MHz): δ 7.48 (dd, J=8.5, 5.5 Hz, 2H), 7.25 (m, 1H), 7.09 (s, 2H), 7.00 (m, 3H), 6.90 (m, 1H). $^{13}$C NMR (CDCl$_3$, 75 MHz): δ 162.8 (d, J=248.3 Hz), 159.2 (d, J=190.6 Hz), 156.0 (d, J=192.8 Hz), 132.9 (d, J=3.0 Hz), 130.7 (d, J=4.3 Hz), 128.3 (d, J=8.0 Hz), 126.5 (m), 119.7 (s), 116.8 (dd, J=25.3, 8.9 Hz), 115.7 (d, J=21.8 Hz), 115.1 (dd, J=24.6, 8.9 Hz), 112.7 (dd, J=24.7, 3.0 Hz). $^{19}$F (CDCl$_3$, 282 MHz): δ−111.5 (s, 1F), −117.4 (d, J=17.0 Hz, 1F), −122.5 (d, J=16.9 Hz, 1F). HRMS (EI) calcd for $C_{14}H_9F_3$ [M]$^+$: 234.0656; found, 234.0659.

(E)-1,2-Dimethoxy-3-(4-methylstyryl)benzene 48: 92% yield, white crystals; mp 38-40° C.; $^1$H NMR (CDCl$_3$, 300 MHz): δ 7.43 (d, J=7.7 Hz, 2H), 7.41 (d, J=16.7 Hz, 1H), 7.22 (d, J=7.8 Hz, 1H), 7.14 (d, J=7.9 Hz, 2H), 7.08 (d, J=16.6 Hz, 1H), 7.02 (t, J=8.2 Hz, 1H), 6.79 (d, J=7.3 Hz, 1H), 3.83 (s, 6H), 2.34 (s, 3H). $^{13}$C NMR (CDCl$_3$, 75 MHz): δ 153.1, 146.8, 137.5, 134.9, 131.7, 129.8, 129.3, 126.6, 124.1, 121.9, 117.8, 111.1, 61.0, 55.7, 21.2. HRMS (EI) calcd for $C_{17}H_{18}O_3$ [M]$^+$: 270.1256; found, 270.1258.

(E)-1-Methoxy-2-(3-methoxystyryl)benzene 49: 86% yield, white crystals; mp 49-50° C.; $^1$H NMR (CDCl$_3$, 300 MHz): δ 7.55 (d, J=7.6 Hz, 1H), 7.48 (d, J=16.5 Hz, 1H), 7.23 (t, J=7.7 Hz, 1H), 7.18 (t, J=7.4 Hz, 1H), 7.09 (d, J=8.9 Hz, 1H), 7.06 (d, J=16.6 Hz, 1H), 7.05 (s, 1H), 6.92 (t, J=7.4 Hz, 1H), 6.83 (d, J=8.2 Hz, 1H), 6.76 (dd, J=8.0, 1.9 Hz, 1H), 3.80 (s, 3H), 3.76 (s, 3H). $^{13}$C NMR (CDCl$_3$, 75 MHz): δ 159.8, 156.9, 139.4, 129.5, 128.9, 128.7, 126.4, 126.2, 123.8, 120.7, 119.3, 113.0, 111.7, 110.9, 55.4, 55.1. HRMS (EI) calcd for $C_{16}H_{16}O_2$ [M]$^+$: 240.1150; found, 240.1156.

(E)-1,4-Dimethoxy-2-(3-methoxystyryl)benzene 50: 96% yield, white crystals; mp 48-49° C.; $^1$H NMR (CDCl$_3$, 300 MHz): δ 7.44 (d, J=16.4 Hz, 1H), 7.24 (t, J=7.9 Hz, 1H), 7.10 (m, 3H), 7.05 (d, J=16.4 Hz, 1H), 6.78 (m, 3H), 3.81 (s, 3H), 3.80 (s, 3H), 3.78 (s, 3H). $^{13}$C NMR (CDCl$_3$, 75 MHz): δ 159.9, 153.8, 151.5, 139.3, 129.5, 129.2, 127.1, 123.6, 119.4, 113.8, 113.2, 112.3, 111.8, 111.7, 56.2, 55.7, 55.2. HRMS (EI) calcd for $C_{17}H_{18}O_3$ [M]: 270.1256; found, 270.1258.

(E)-1,2-Dimethoxy-3-(4-(trifluoromethyl)styryl)benzene 54: 84% yield, white crystals; mp 67-69° C.; $^1$H NMR (CDCl$_3$, 300 MHz): δ 7.62 (d, J=9.3 Hz, 2H), 7.59 (d, J=9.7 Hz, 2H), 7.54 (d, J=16.7 Hz, 1H), 7.24 (d, J=7.8 Hz, 1H), 7.13 (d, J=16.6 Hz, 1H), 7.07 (t, J=8.0 Hz, 1H), 6.87 (d, J=8.0 Hz, 1H), 3.88 (s, 3H), 3.87 (s, 3H). $^{13}$C NMR (CDCl$_3$, 75 MHz): δ 153.1, 147.3, 141.2, 130.9, 128.3, 126.7, 125.6, 125.5, 124.2, 118.0, 112.0, 61.3, 56.0. $^{19}$F (CDCl$_3$, 282 MHz): δ−60.9 (s, 3F). HRMS (EI) calcd for $C_{17}H_{15}F_3O_2$ [M]$^+$: 308.3002; found, 308.3000.

(E)-1-(4-Isopropylstyryl)-2,3-dimethoxybenzene 55: 96% yield, oil; $^1$H NMR (CDCl$_3$, 300 MHz): δ 7.35 (d, J=8.2 Hz, 2H), 7.26 (d, J=16.5 Hz, 1H), 7.24 (dd, J=6.3, 1.6 Hz, 1H), 7.17 (d, J=8.1 Hz, 2H), 7.14 (d, J=16.5 Hz, 1H), 7.07 (t, J=8.0 Hz, 1H), 6.84 (dd, J=8.1, 1.2 Hz, 1H), 3.89 (s, 3H), 3.87 (s, 3H), 2.94 (sept, J=6.9 Hz, 1H), 1.30 (d, J=6.9 Hz, 6H). $^{13}$C NMR (CDCl$_3$, 75 MHz): δ 153.1, 148.5, 146.8, 135.3, 131.8, 129.8, 126.7, 126.6, 124.1, 122.0, 117.8, 111.1, 61.0, 55.7, 33.9, 23.9. HRMS (EI) calcd for $C_{19}H_{22}O_2$ [M]$^+$: 282.1620; found, 282.1618.

Activation of Nrf2 by Trans-Stilbenes (Analogs of Resveratrol) and Dienone Analogues of the Natural Product Curcumin As shown in FIGS. 2-5, numerous trans-stilbene analogs of resveratrol activate Nrf2. In addition, numerous analogues of also curcumin activate Nrf2. Many of these analogues also inhibit NF-kB. See, Deck, et al., European J. Med. Chem. 2018 Jan. 1; 143:854-865. However, the number of analogues of resveratrol (i.e., the trans stilbenes) and analogues of curcumin (i.e., dienones) that are both potent inhibitors of NF-kB and potent activators of Nrf2 is limited. FIG. 6 shows the structures of the trans stilbenes and dienones that are most potent as dual target analogues. All are much more potent than resveratrol or curcumin and useful in cosmetic compositions pursuant to the present invention.

Further Examples

The following exemplary compositions are prepared using components as set forth below. All components are included in % wt/v. Compounds which are presented above and in the attached FIGS. 2-6 are particularly useful in the present invention to provide cosmetic compositions exhibiting unique activity as otherwise described herein.

All Amounts in % wt/v

Face Cleanser/Face Toner Composition
  Active trans-stilbene/dienone (such as LD55) 0.05-5%, preferably 0.1%-2.0% Fractionated
  Coconut oil 5%-50%
  Avocado oil 5%-50%
  Almond oil 5%-25%
  Vitamin E 0.1%-10%
  Rosehip 0.1%-15%
  Frankincense 0.001%-2%
  Lavender 001%-2%
  Melaleuca 001%-2%
  Peppermint 001%-2%

Facial Serum for Rejuvenating and/or Beautifying the Skin
  Active trans-stilbene/dienone (such as LD55) 0.05-5%, preferably 0.1%-2.0% Fractionated
  Coconut oil 5%-50%
  Argan oil—1%-30%
  Jojoba oil—25%-75%

Vitamin E 0.1%-10%
Frankincense 0.001%-2%
Lavender 001%-2%
Melaleuca 001%-2%
Peppermint 001%-2%

Body Moisturizer or Rejuvenating and/or Beautifying Skin
  Active trans-stilbene/dienone (such as LD55) 0.05-5%, preferably 0.1%-2.0% Fractionated
  Coconut oil 5%-50%
  Jojoba oil—25%-75%
  Argan oil—1%-30%
  Almond oil 5-%-25%
  Vitamin E 0.1%-10%
  Rosemary oil 0.1%-15%
  Frankincense 0.001%-2%
  Lavender 001%-2%
  Melaleuca 001%-2%
  Peppermint 001%-2%

Serum, Lotion, Solution, Cream or Salve for Resolving Skin Imperfections, Smoothing Skin and Treating Acne Scars and Other Scars, Including Hard to Resolve Scars and Stretch Marks
  Active trans-stilbene/dienone (such as LD55) 0.05-5%, preferably 0.1%-2.0
  Fractionated coconut oil 5%-50%
  Argan oil—1%-30%
  Jojoba oil—25%-75%
  Vitamin E 0.1%-10%
  Frankincense 0.001%-2%
  Lavender 001%-2%
  Melaleuca 001%-2%
  Peppermint 001%-2%

Wash for Treating Acne and Acne Scars and Smoothing Bumps and Irregularities in Skin
  Active trans-stilbene/dienone (such as LD55) 0.05-5%, preferably 0.1%-2.0%
  Argan oil—1%-30%
  Grape seed oil—1%-50
  Cucumber oil—1-50%
  Elderberry oil 1%-50%
  Jojoba oil—25%-75%
  Vitamin E 0.1%-10%
  Melaleuca 001%-2%
  Rosehip—0.001-25%
  Watermelon oil 0.001-25%
  Peppermint 001%-2%
  Cucumber essential oil—0.001-2%

Moisturizer for Treating Acne and Acne Scars and Smoothing Bumps and Irregularities in Skin
  Active trans-stilbene/dienone (such as LD55) 0.05-5%, preferably 0.1%-2.0%
  Argan oil—1%-30%
  Grape seed oil—1%-50
  Cucumber oil—1-50%
  Elderberry 1%-50%
  Jojoba oil—25%-75%
  Vitamin e 0.1%-10%
  Melaleuca 001%-2%
  Rosehip—0.001-25%
  Watermelon oil 0.001-25%
  Peppermint 001%-2%
  Cucumber essential oil—0.001-2%
  Shea butter—10%-30% w/v
  Beeswax—10%-30% w/v Moisturizing Composition for Treating Rough and Damaged Skin
  Active trans-stilbene/dienone (such as LD55) 0.05-5%, preferably 0.1%-2.0%
  Fractionated Coconut oil 5%-50%
  Jojoba oil—25%-75%
  Almond oil 5-%-25%
  Vitamin E 0.1%-10%
  Frankincense 0.001%-2%
  Lavender 001%-2%
  Melaleuca 001%-2%
  Peppermint 001%-2%
  Shea butter—10%-30% w/v
  Beeswax—10%-30% w/v Cream or Polish for Teating Nails to Repair Damaged, Cracked and/or Discolored Nail/Ungual Tissue
  Active trans-stilbene/dienone (such as LD55) 0.05-5%, preferably 0.1%-2.0%
  Fractionated Coconut oil 5%-50%
  Jojoba oil—25%-75%
  Almond oil 5-%-25%
  Vitamin E 0.1%-10%
  Frankincense 0.001%-2%
  Lavender 001%-2%
  Melaleuca 001%-2%
  Peppermint 001%-2%
  Shea butter—10%-30% w/v
  Beeswax—10%-30% w/v After Shave Lotion
  Active trans-stilbene/dienone (such as LD55) 0.05-5%, preferably 0.1%-2.0%
  Fractionated Coconut oil 5%-50%
  Jojoba oil—25%-75%
  Argan oil—1%-30%
  Almond oil 5-%-25%
  Vitamin E 0.1%-10%
  Rosemary oil 0.1%-15%
  Frankincense 0.001%-2%
  Lavender 001%-2%
  Melaleuca 001%-2%
  Peppermint 001%-2%

Serum for Treating Wrinkles and Toning Skin
  Active trans-stilbene/dienone (such as LD55) 0.05-5%, preferably 0.1%-2.0%
  Coconut 5%-50%
  Argan oil—1%-30%
  Jojoba oil—25%-75%
  Vitamin E 0.1%-10%
  Frankincense 0.001%-2%
  Lavender 001%-2%
  Melaleuca 001%-2%
  Peppermint 001%-2%

Lotion for Treatment of Environment Toxins and Resulting Rashes
  Active trans-stilbene/dienone(such as LD55) 0.05-5%, preferably 0.1%-2.0%
  Fractionated Coconut oil 5%-50%
  Jojoba oil—25%-75%
  Almond oil 5-%-25%
  Vitamin E 0.1%-10%
  Frankincense 0.001%-2%
  Lavender 001%-2%
  *Melaleuca* 001%-2%
  Peppermint 001%-2%
  Shea butter—10%-30% w/v
  Beeswax—10%-30% w/v Hand Lotion/Eland Cream for Cleansing Hands
  Active trans-stilbene/dienone (such as LD55) 0.05-5%, preferably 0.1%-2.0%

Fractionated Coconut oil 5%-50%
Jojoba oil—25%-75%
Almond oil 5-%-25%
Vitamin E 0.1%-10%
Frankincense 0.001%-2%
Lavender 001%-2%
*Melaleuca* 001%-2%
Peppermint 001%-2%
Shea butter—10%-30% w/v
Beeswax—10%-30% w/v Cream or Lotion for Treating Warts, Removing Skin Tags and Smoothing Skin Irregularities
Active trans-stilbene/dienone (such as LD55) 0.05-5%, preferably 0.1%-2.0%
Fractionated Coconut oil 5%-50%
Jojoba oil—25%-75%
Almond oil 5-%-25%
Vitamin E 0.1%-10%
Frankincense 0.001%-2%
Lavender 001%-2%
*Melaleuca* 001%-2%
Peppermint 001%-2%
Shea butter—10%-30% w/v
Beeswax—10%-30% w/v Cosmetic Composition
All Amounts are in % wt/v
Coconut Oil—10-50%
Jojoba Oil—15-75%
Argan Oil 2-25%
Vitamin E (30,000 IU) 0.01-1.5%
Melaleuca Essential Oil 0.1-15 drops/110 mL
Lavender Essential Oil 0.1-15 drops/110 mL
Frankincense Essential Oil 0.1-15 drop/110 mL
LD55 0.1-2.5% w/v The above composition was prepared and was utilized on certain problem issues to determine what efficacy the compounds exhibited. The composition was applied to the skin of several individuals (as indicated by their initials). The compositions resolved the following cosmetic issues.

KT—Wrinkles & acne scars 20 ml
DT—Scars and Wrinkles 10 nil
K—Cracked skin, eczema, dry skin 30 ml
E—Eczema and dry skin 15 ml—did not work well (marginal effecte) which was attributed to the application of apple cider vinegar which was causing flareup. Resolution of this toxicity should resolve the issue going forward.
A—Stretch marks 10 ml.
V—Hard to Revolve wounds (wounds that wont heal) 15 ml.
K—Eczema/non-healing wounds
Several Children (age 12 or less)—hard to resolve wounds—20 ml.
L—Wrinkles
T—Cracked heel/foot-full resolution.

Figure 12:
FIG. 12 shows the treatment of a difficult to treat wound after approximately 36 hours of treatment.
Figure 14:
FIG. 14 shows the effect of skin smoothing and beautiful in a female subject after 63 days.
Figure 15:
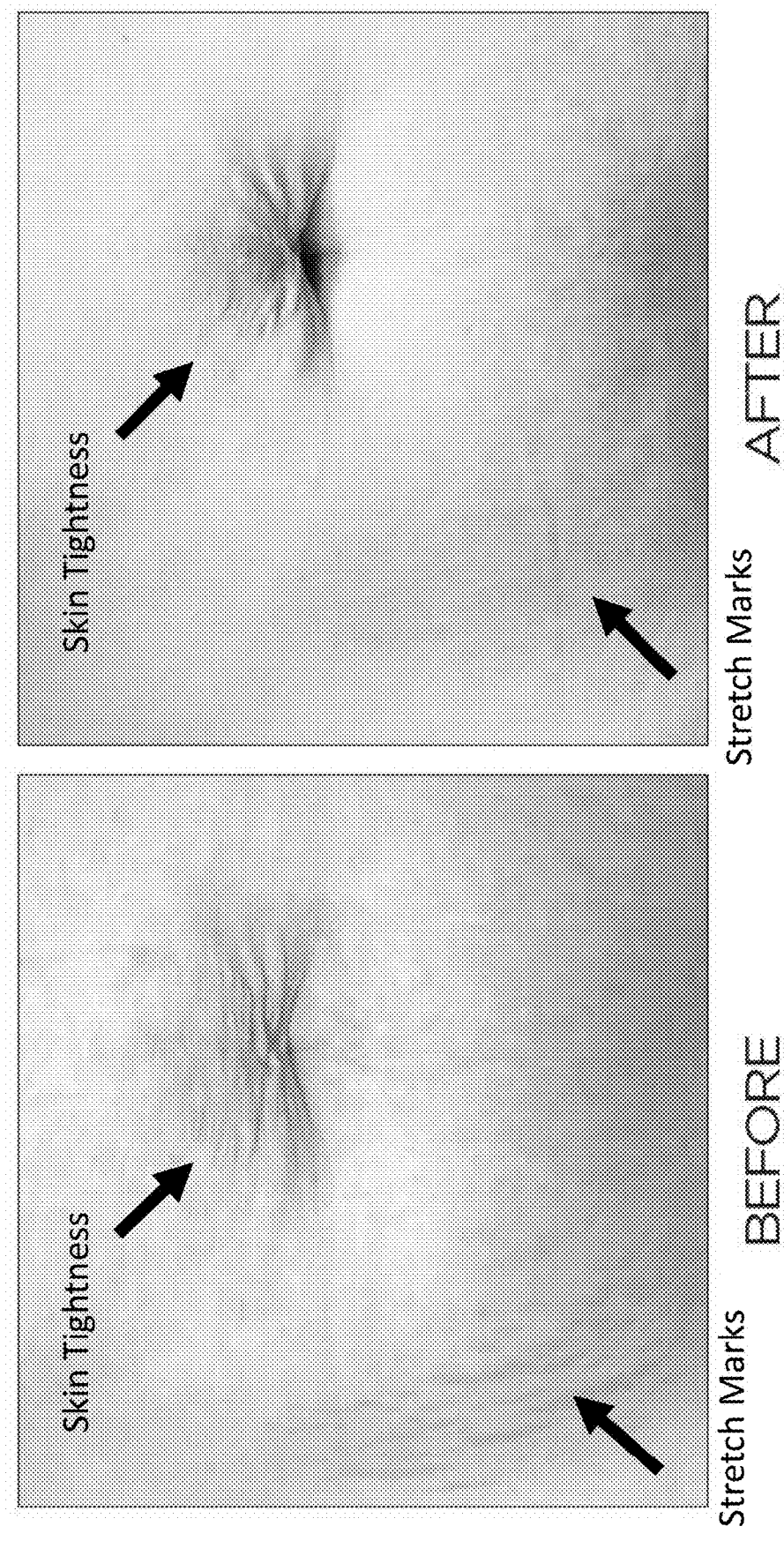
Figure 16:
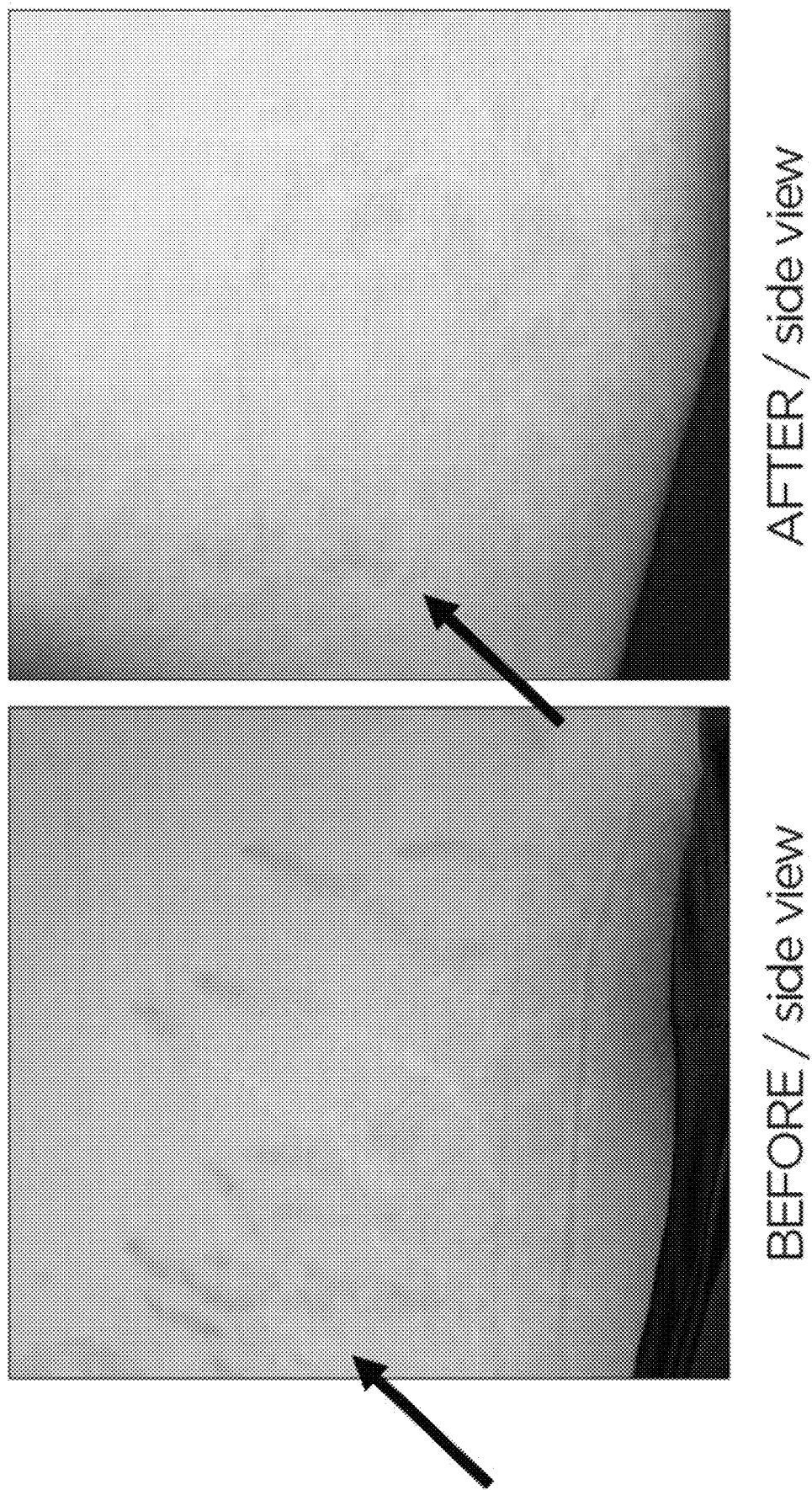
Figure 18:
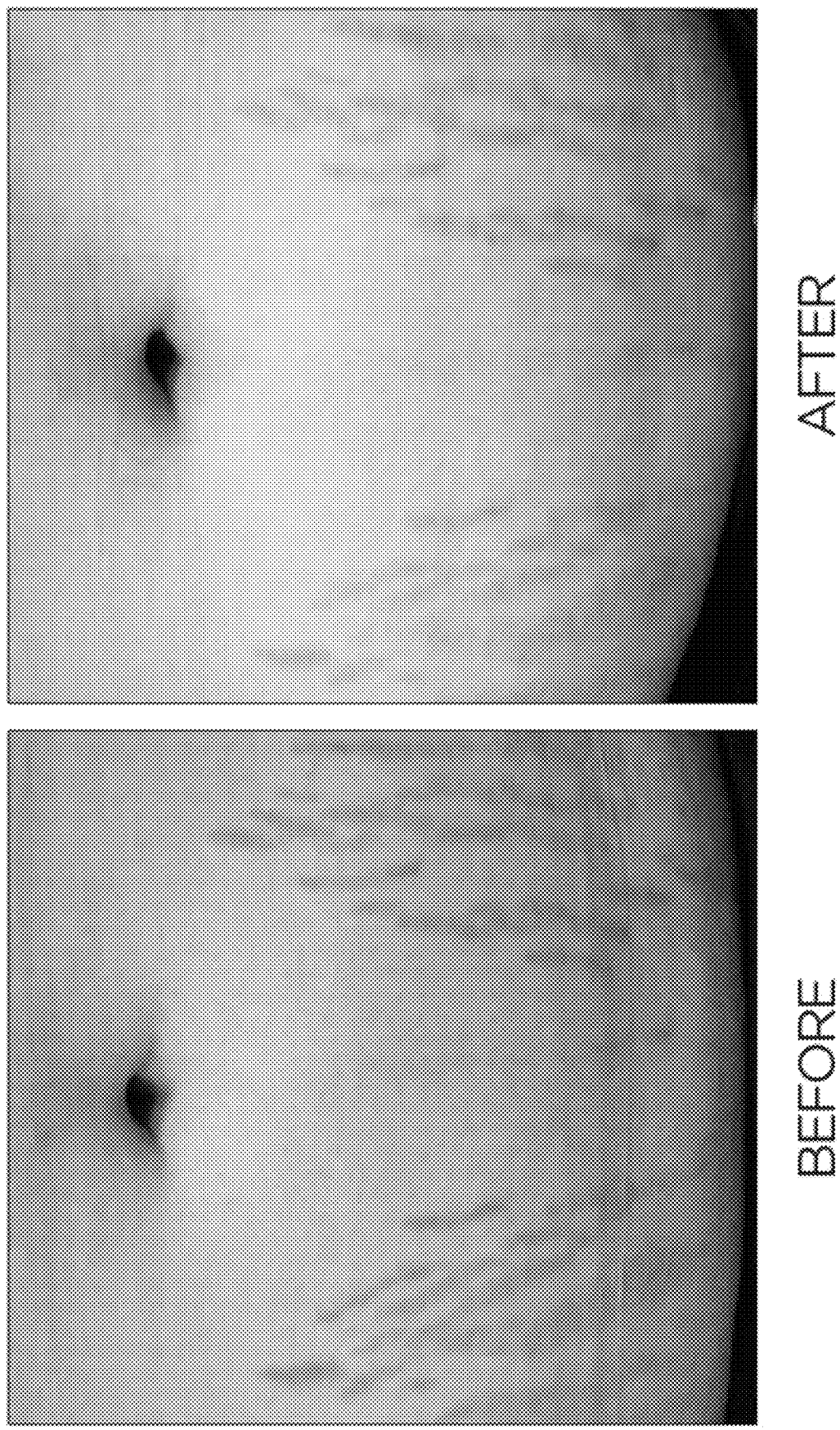
FIG. 18 shows that stretch marks were substantially reduced and lightened when treated with serum containing LD55 for 30 days. In this example, the co-inventors are continuing treatment of this individual for 90 days since the stretch marks were significantly greater than for other subjects.
Figure 19:
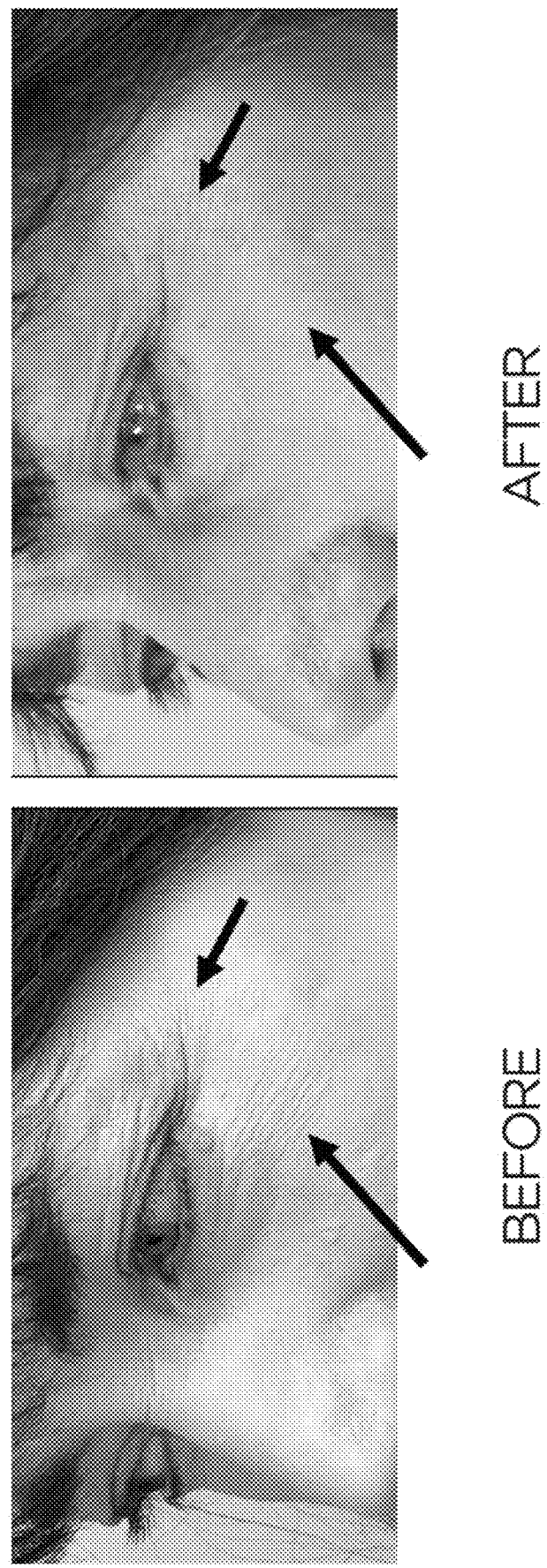
Figure 21:
FIG. 21 shows the effect on an otherwise untreatable wound on the forehead of a subject which was treated with serum containing LD55 for 30 days.
Figure 22:
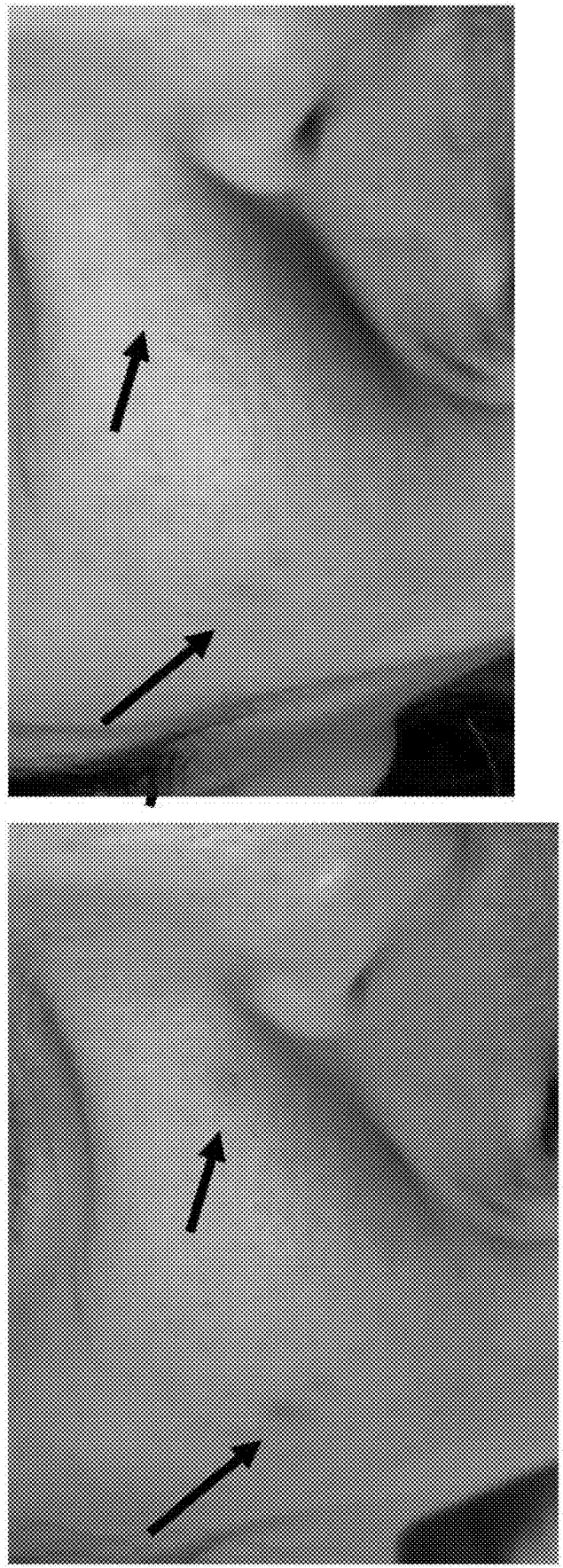
FIG. 22 shows the effect on acne scars and redness on the face of a subject treated with serum containing LD55 for 30 days.

FIGS. 7-23 show the dramatic effect of the composition on several subjects in the treatment of wrinkles (FIGS. 7, 8, 9, 11, 19), acne scars (FIG. 10), acne scars/skin coloration (FIG. 22), hard to heal wounds (FIGS. 12, 21), skin smoothing and beautification (FIGS. 13, 14, 20), stretch marks and skin tightness (FIG. 15), stretch marks (FIGS. 16-18) and skin rejuvenation (FIG. 23).

Conclusion—the cosmetic compositions according to the present invention are particularly useful in resolving a number of skin conditions and cosmetic concerns thought to be very difficult to resolve and show particularly effective activity with respect to same.

REFERENCES—FIRST SET

1. Guerreiro, R. J.; Hardy, J. Biochem. Soc. Trans. 2011, 39, 910.
2. Bales, K. R. Expert Opin. Drug Discov. 2012, 7, 281.
3. Fischer, O. Z. Gesamte. Psychiatr. 1910, 3, 371.
4. McGeer, E. G.; McGeer, P. L. J. Alzheimers Dis. 2010, 19, 355.
5. Alexander, J. J.; Anderson, A. J.; Barnum, S. R.; Stevens, B.; Tenner, A. J. J. Neurochem. 2008, 107, 1169.
6. Joshi, G.; Johnson, J. A. Recent Pat. CNS Drug Discov. 2012, 7, 218.
7. Sandberg, M.; Patil, J.; D'Angelo, B.; Weber, S. G.; Mallard, C. Neuropharmacology 2014, 79, 298.
8. Cardozo L. F.; Pedruzzi, L. M.; Stenvinkel, P.; Stockler-Pinto, M. B.; Daleprane, J. B.; Leite Jr, M.; Mafra, D. Biochemie 2013, 95, 1525.
9. Ruiz, S.; Pergola, P. E.; Zager, R. A.; Vaziri, N. D. Kidney Int. 2013, 83, 1029.
10. Wakabayashi, N.; Slocum, S. L.; Skoho, J. J.; Shin, S.; Kensler, T. W. Antioxid. Redox Signal. 2010, 13, 1649.
11. Ganesh Yerra, V.; Negi, G.; Sharma, S. S.; Kumar, A. Redox Biology 2013, 1, 394.
12. Hybertson, B. M.; Gao, B.; Bose, S. K.; McCord, J. M. Mol. Aspects Med. 2011, 32, 234.
13. Zhang, J.; Wang, X.; Vikash, V.; Ye, Q.; Wu, D.; Liu, Y.; Dong, W. Oxid. Med. Cell. Longev. 2016, Epub ahead of print.
14. Kumar, H.; Kim, I-S.; More, S. V.; Kim, B-W.; Choi, D-K. Nat. Prod. Rep. 2014, 31, 109.
15. Rojo, A. I.; Innamorato, N. G.; Martin-Moreno, A. M.; De Ceballos, M. L.; Yamamoto, M.; Cuadrado, A. Glia 2010, 58, 588.
16. Shih, A. Y.; Li, P.; Murphy, T. H. J. Neurosci. 2005, 25, 10321.
17. Jin, W.; Wang, H.; Yan, W.; Zhu, L.; Hu, Z.; Ding, Y.; Tang, K. J. Neurotrauma 2009, 26, 131.
18. Kraft, A. D.; Johnson, D. A.; Johnson, J. A. J. Neurosci. 2004, 24, 1101.
19 Ramsey, C. P.; Glass, C. A.; Montgomery, M. B.; Lindl, K. A.; Ritson, G. P.; Chia, L. A.; Hamilton, R. L.; Chu, C. T,; Jordan-Sciutto, K. L. J. Neuropathol. Exp. Neurol. 2007, 66, 75.
20. Solberg, N. O.; Chamberlin, R.; Vigil, J. R.; Deck, L. M.; Heidrich, J. E.; Brown, D. C.; Brady, C. I.; Vander Jagt, T. A.; Garwood, M.; Bisoffi, M.; Severns, V.; Vander Jagt, D. L.; Sillerud, L. O. J. Alzheimers Dis. 2014, 40, 191.
21. Heynekamp, J. J.; Weber, W. W.; Hunsaker, L. A.; Gonzales, A. M.; Orlando, R. A.; Deck, L. M.; Vander Jagt, D. L. J. Med. Chem. 2006, 49, 7182.
22. Diaz-Gerevini, G. T.; Repossi, G.; Dain, A.; Tarres, M. C.; Das, U. N.; Eynard, A. R. Nutrition 2016, 32, 174.
23. Houghton, C. A.; Fassett, R. G.; Coombes, J. S. Nutr. Rev. 2013, 71,709.
24. (a) Homer, L.; Hoffman, H.; Wippel, H. G.; Klahre, G. Chem. Ber. 1959, 92, 2499 (b) Wadsworth, W. S. Jr.; Emmons, W. D. J. Am. Chem. Soc. 1961, 83, 1733.
25. Das, J.; Pany, S.; Majhi, A. Bioorg. Med. Chem. 2011, 19, 5321
26. Arbuzov, B. A. Pure Appl. Chem. 1964, 9, 307.
27. Rivera, H.; Morales-Rios, M. S.; Bautista, W.; Shibayama, M.; Tsutsumi, V.; Muriel, P.; Perez-Alvarez, V. Can. J. Physiol. Pharmacol. 2011, 89, 759.
28. Yunes, S.; Tchani, G.; Baziard-Mouysset, G.; Stigliani, J. L.; Payard, M.; Bonnafous, R.; Tisne-Versailles, J. Eur. J. Med. Chem. 1994, 29, 87.

29. Zhang, X.; Zeng, W.; Yang, Y.; Huang, H.; Liang, Y. Synlett 2013, 24, 1687
30. Gust, R.; Schoenenberger, H. Arch. Pharmazie, 1995, 328, 595.
31. Cao, C.; Sheng, B.; Chen, G. J. Phys. Org. Chem Gust, R.; Schoenenberger, H. Arch. Pharmazie. 2012, 25, 1315.
32. Kang, S.; Cuendet, M.; Endringer, D. C.; Croy, V. L.; Pezzieto, J. M.; Lipton, M. A. Bioorg. Med. Chem. 2009, 17, 1044.
33. Sun, B.; Hoshino, J.; Jermihov, K.; Marlero, L.; Pezzuto, J. M.; Mesecar, A. D.; Cushman, M. Bioorg. Med. Chem. 2010, 18, 5352.
34. Lion, C.; Matthews, C. S.; Stevens, M. F. G.; Westwell, A. D. J. Med. Chem. 2005, 48, 1292.
35. Dunne, E. C.; Coyne, E. J.; Crowley, P. B.; Gilheany, D. G. Tetrahedron Lett. 2002, 43, 2449.
36. Buu-Hoi, N. P.; Xuong, N. D.; Diep, B. K.; Quang, N. N. J. Org. Chem. 1962, 27, 2669.
37. Zhang, M.; Jia, T.; Sagamanova, I. K.; Pericas, M. A.; Walsh, P. J. Org. Lett. 2015, 17, 1164.
38. Karki, S. S.; Bhutle, S. R.; Sahoo, S.; Reddy, R.; Balzarini, J.; De Clercq, E.; Darji, S. Y. Med. Chem. Res. 2011, 20, 1349.
39. Karke, S. S.; Bhutle, S. R.; Pedgaonkar, G. S.; Zubaidha, P. K.; Shaikh, R. M.; Rajput, C. G.; Shendarkar, G. S. Med. Chem. Res. 2011, 20, 1158.
40. Chalal, M.; Vervandier-Fasseur, D.; Meunier, P.; Cattey, H.; Hierso, J-C. Tetrahedron 2012, 68, 3899.
41. Ao, J.; Chen, Y.; Xu, X.; Zhang, X.; Yu, Y.; Yu, P.; Hua, E. Asian J. Chem. 2014, 26, 2092.
42. Saiyed, A. S.; Patel, K. N.; Kamath, B. V.; Bedekar, A. V. Tetrahedron Lett. 2012, 53, 4692.
43. Motoshima, K.; Sugita, K.; Hashimoto, Y.; Ishikawa, M. Bioorg. Med. Chem. Lett. 2011, 21, 3041.
44. Khandelwal, M.; Hwang, I.; Nair, P. C.; Lee, J-W. Bull. Korean Chem. Soc. 2012, 33, 1190.
45. Hayes, J. D.; Dinkova-Kostova, A. T. Trends Biochem. Sci. 2014, 39, 199.
46. Kuma, H.; Kim, I-S.; More, S. V.; Kim, B-W.; Choi, D-K. Nat. Prod. Rep. 2014, 31, 109.
47. Zhang, D. D.; Hannink, M. Mol. Cell. Biol. 2003, 23, 8137.
48. Keum, Y-S.; Choi, B. Y. Molecules 2014, 19, 10074.
49. Magesh, S.; Chen, Y.; Hu, L. Med. Res. Rev. 2012, 32, 687.
50. Chin, M. P.; Wrolstad, D.; Bakris, G. L.; Chertpw, G. M.; De Zeeuw, D.; Goldberry, A.; Linde, P. G.; McCullough, P. A.; McMurry, J. J.; Wittes, J.; Meyer, C. J. J. Cardiac Fail. 2014, 20, 953.
51. Bomprezzi, R. Ther. Adv. Neurol. Disord. 2015, 8, 20.
52. Yore, M. M.; Kettenbach, A. N.; Sporn, M. B.; Gerber, S. A.; Liby, K. T. PLoS One, 2011, 6, e22862.
53. Richardson, B. G.; Jain, A. D.; Speltz, T. E.; Moore, T. W. Bioorg. Med. Chem. Lett. 2015, 25, 2261.
54. Cleasby, A.; Yon, J.; Day, P. J.; Richardson, C.; Tickle, I. J.; Williams, P. A.; Callahan, J. F.; Carr, R.; Concha, N.; Kerns, J. K.; Qi, H.; Sweitzer, T.; Ward, P. Davies, T. G. PLoS One 2014, 9, e98896.
55. Li, X.; Zhang, D.; Hannink, M.; Beamer, L. J. J. Biol. Chem. 2004, 24, 279.
56. Lo, S. C; Li, X.; Henzl, M. T.; Beamer, L. J.; Hannink, M. EMBO J. 2006, 25, 3605.
57. Hancock, R.; Bertrand, H. C.; Tsujita, T.; Naz, S.; El-Bakry, A.; Laoruchupong, J.; Hayes, J. D.; Wells, G. Free Radic. Biol. Med. 2012, 52, 444.
58. Steel, R.; Cowan, J.; Payerne, E.; O'Connell, M. A.; Searcey, M. ACS Med. Chem. Lett. 2012, 3, 407.
59. Hu, L.; Magesh, S.; Chen, L.; Lewis, T. A.; Chen, Y.; Khodier, C.; Inoyama, D.; Beamer, L. J.; Emge, T. J.; Shen, J.; Kerrigan, J. E.; Kong, A. N.; Dandapani, S.; Palmer, M.; Schreiber, S. L.; Munoz, B. Bioorg. Med. Chem. Lett. 2013, 23, 3039.
60. Jnoff, E.; Albrecht, C.; Barker, J. J.; Barker, O.; Beaumont, E.; Bromidge, S.; Brookfield, F.; Brooks, M.; Bubert, C.; Ceska, T.; Corden, V.; Dawson, G.; Duclos, S.; Fryatt, T.; Genicot, C. Jigorel, E.; Kwong, J.; Maghames, R.; Mushi, I.; Pike, R.; Sands, Z. A.; Smith, M. A.; Stimson, C. C.; Courade, J. P. ChemMedChem. 2014, 9, 699.
61. Marcotte, D.; Zeng, W.; Hus, J-C.; McKenzie, A.; Hession, C.; Jin, P.; Bergeron, C.; Lugovskoy, A.; Enyedy, I.; Cuervo, H.; Wang, D. Atmanene, C.; Roecklin, D.; Vecchi, M.; Vivat, V.; Kraemer, J.; Winkler, D.; Hong, V.; Chao, J.; Lukashev, M.; Silvian, L. Biorg. Med. Chem. 2013, 21, 4011.
62. Sun, H-P.; Jiang, Z-Y.; Zhang, M-Y.; Lu, M-C.; Yang, T-T.; Pan, Y.; Huang, H-Z.; Zhang, X-J.; You, Q-D. MedChemComm 2014, 5, 93.
63. Wu, T. Y.; Khor, T. O.; Su, Z. Y.; Saw, C. L.; Shu, L.; Cheung, K. L.; Huang, Y.; Yu, S.; Kong, A. N. AAPS J. 2013, 15, 864.
64. Ma, Q.; Kinneer, K.; Bi, Y.; Chan, J. Y.; Kan, Y. W. Biochem. J. 2004, 377, 205.
65. Kwak, M-K.; Itoh, K.; Yamamoto, M.; Kensler, T. W. Mol. Cell. Biol. 2002, 22, 2883.
66. Rushworth, S. A.; Zaitseva, L.; Murray, M. Y.; Shah, N. M.; Bowles, K. M.; MacEwan, D. J. Blood 2012, 120, 5188.
67. Lau, A.; Wang, X-J.; Zhao, F.; Villeneuve, N. F.; Wu, T.; Jiang, T.; Sun, Z.; White, E.; Zhang, D. D. Mol. Cell. Biol. 2010, 30, 3275.
68. Ichimura, Y.; Waguri, S.; Sou, Y.; Kageyama, S.; Hasegawa, J.; Ishimura, R.; Saito, T.; Yang, Y.; Kouno, T.; Fukutomo, T.; Hoshii, T.; Hirao, A.; Takagi, K.; Mizushima, T.; Motohashi, H.; Lee, M. S.; Yoshimori, T.; Tanaka, K.; Yamamoto, M.; Komatsu, M. Mol. Cell 2013, 51, 618.
69. Tebay, L. E.; Robertson, H.; Durant, S. T.; Vitale, S. R.; Penning, T. M.; Dinkova-Kostova, A. T.; Hayes, J. D. Free Radic. Biol. Med. 2015, 88, 108.

REFERENCES—SECOND SET

1. Chen, J., et al., *Natural Terpenes as Penetration Enhancers for Transdermal Drug Delivery*. Molecules, 2016. 21(12).
2. Heynekamp, J. J., et al., *Substituted trans-stilbenes, including analogues of the natural product resveratrol, inhibit the human tumor necrosis factor alpha-induced activation of transcription factor nuclear factor kappaB*. J Med Chem, 2006. 49(24): p. 7182-9.
3. Deck, L. M., et al., *Activation of anti-oxidant Nrf2 signaling by substituted trans stilbenes*. Bioorg Med Chem, 2017. 25(4): p. 1423-1430.
4. Ranzato, E., S. Martinotti, and B. Burlando, *Wound healing properties of jojoba liquid wax: an in vitro study*. J Ethnopharmacol, 2011. 134(2): p. 443-9.
5. Menke, N. B., et al., *Impaired wound healing*. Clin Dermatol, 2007. 25(1): p. 19-25.
6. Lin, T. K., L. Zhong, and J. L. Santiago, *Anti-Inflammatory and Skin Barrier Repair Effects of Topical Application of Some Plant Oils*. Int J Mol Sci, 2017. 19(1).
7. Nevin, K. G. and T. Rajamohan, *Effect of topical application of virgin coconut oil on skin components and antioxidant status during dermal wound healing in young rats*. Skin Pharmacol Physiol, 2010. 23(6): p. 290-7.

The invention claimed is:

1. A method of treating a cosmetic condition of the keratinous tissue of a subject comprising administering to the subject a composition comprising an effective amount of at least one compound which exhibits dual activity as a NF-KB signaling inhibitor and a Nrf2 signaling agonist, in combination with at least one cosmetic additive, wherein the compound comprises at least one structure selected from the group consisting of:

stilbene which contains at least one substitute on at least one of the aryl rings; dienone; and 3-hydroxy-1,3-diphenylprop-2-en-1-one, wherein the cosmetic condition of the keratinous tissue of the subject comprises at least one condition selected from the group consisting of acne scars, stretch marks, and wrinkles.

2. The method of claim 1, wherein the cosmetic additive is selected from the group consisting of water, an alcohol or other water compatible cosmetically acceptable solvent, a water incompatible solvent, an emollient, a humectant, an oil, a conditioning agent, a surfactant, a thickener/thickening agent, a stiffening agent, an emulsifier, a medicament, a fragrance, a preservative, a deodorant component, an antiperspirant compound, a skin protecting agent, a pigment, a dye, a coloring agent, a preservative and mixtures thereof.

3. The method of claim 1, wherein the compound has a chemical structure selected from the group consisting of:

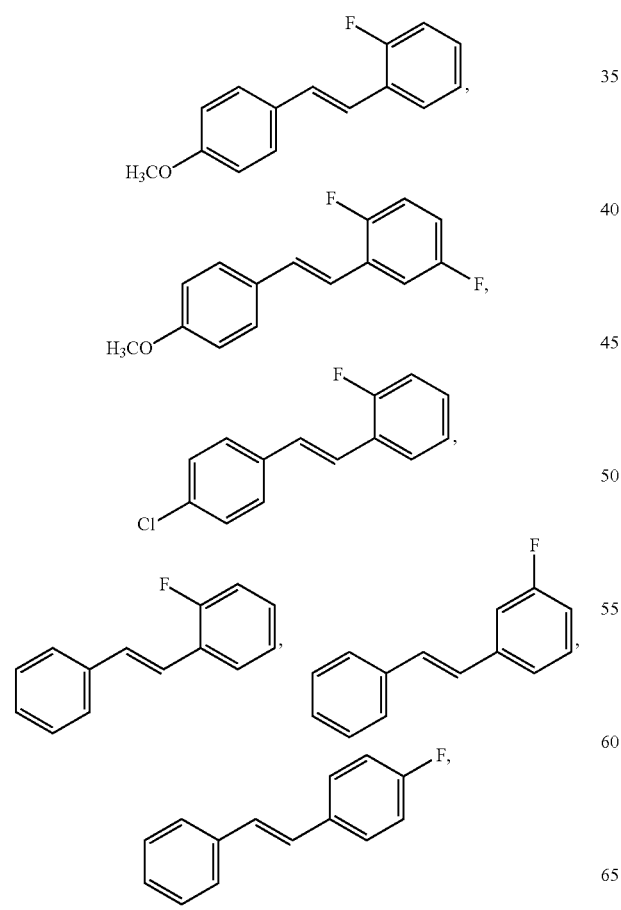

-continued

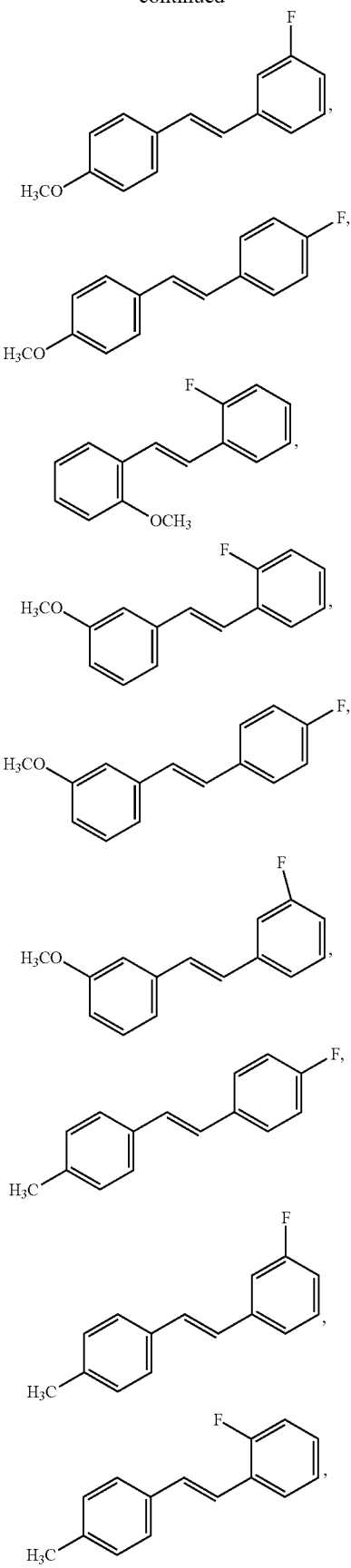

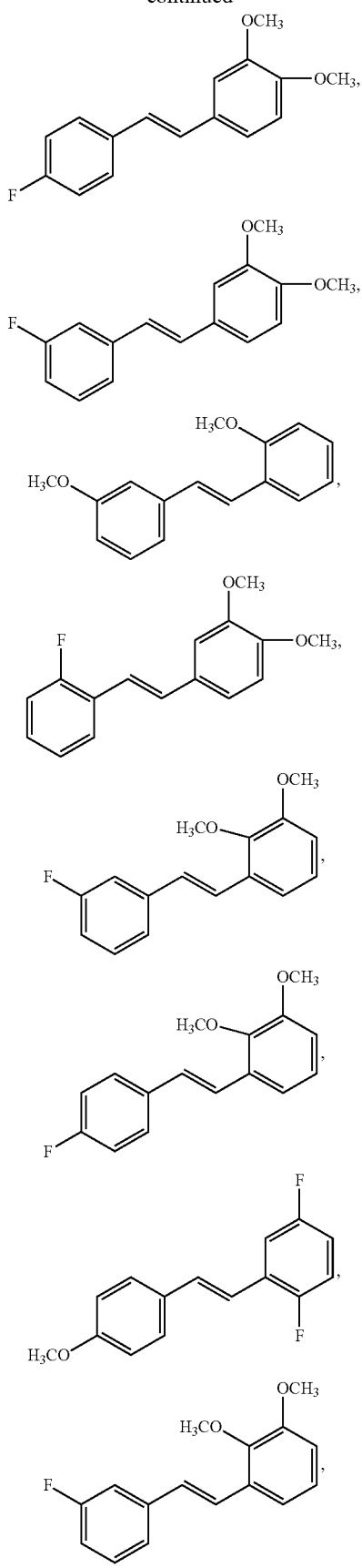
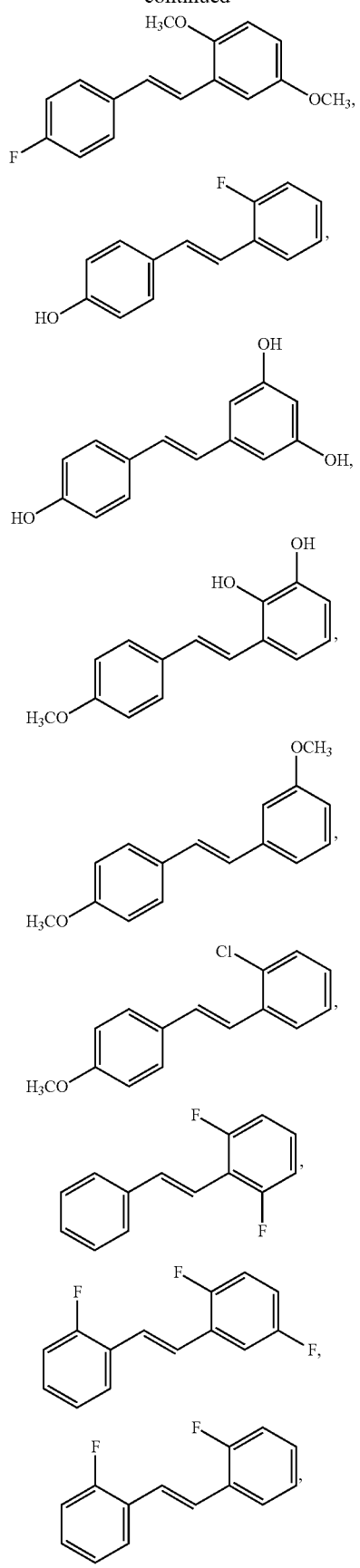

-continued

-continued

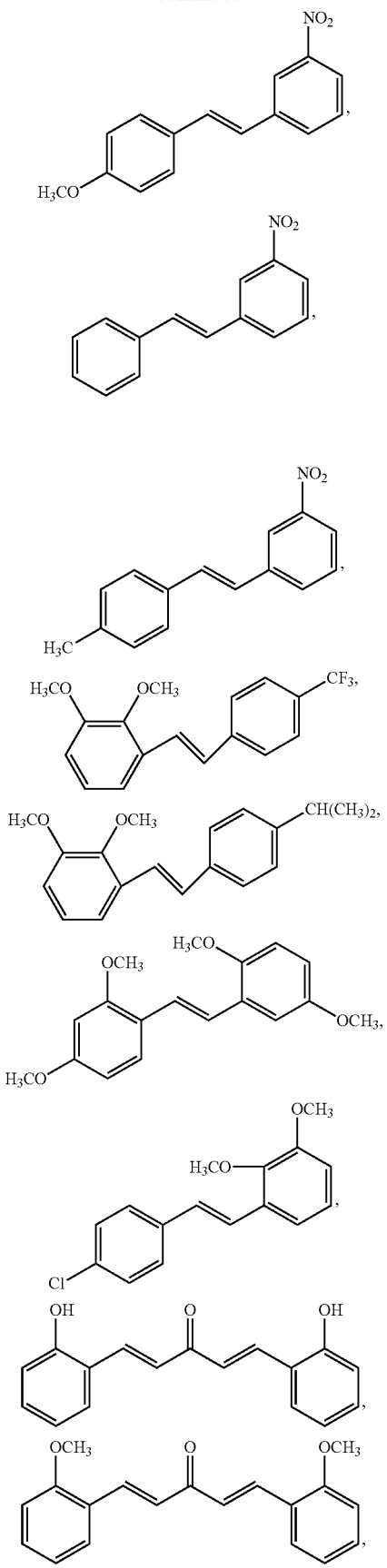

-continued

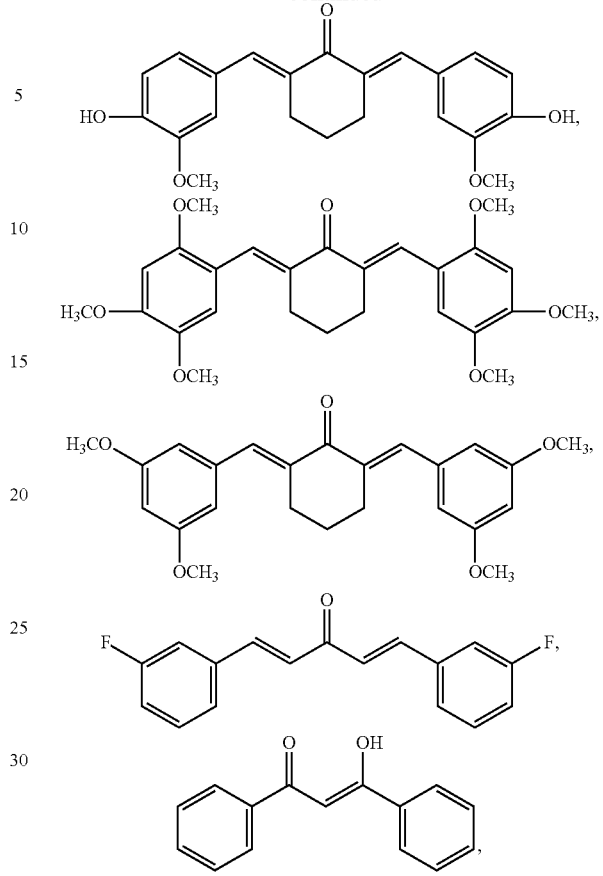

and a pharmaceutically acceptable salt thereof, and a mixture thereof.

4. The method of claim 1, wherein the compound is included in an amount of 0.01-10 wt % of the composition.

5. The method of claim 1, wherein the composition further comprises carrier and essential oils that also have anti-inflammatory and anti-oxidant activity.

6. The method according to claim 5, wherein the carrier and essential oils comprise Jojoba Oil and/or Coconut oil.

7. The method according to claim 5, wherein the carrier and essential oils further comprise skin penetration enhancing terpenes that assist in the delivery of actives in the composition and provide an effective penetration of actives for administration of the composition onto the skin of the subject.

8. The method according to claim 7, wherein said terpene is selected from the group consisting of a-pinene, b-pinene, camphene, b-myrcene, d-3-carene, a-terpinene, cis-ocimene, limonene, p-cymene, trans-ocimene, g-terpinene, terpinolene, linalool, geraniol, b-caryophyllene, cis-nerolidol, trans-nerolidol and mixtures thereof.

9. The method of claim 1, wherein said composition is administered directly to the skin of the subject, and the composition is formulated in a lotion, cream, salve or liquid.

10. The method of claim 1, wherein composition is a pharmaceutical composition and the compound is formulated in admixture with a pharmaceutically acceptable carrier.

11. The method of claim 10, wherein the pharmaceutical composition is administered orally or parenterally.

12. The method of claim 11, wherein a daily dosage of the compound is 0.01 to 500 milligrams per kilogram of body weight per day given in divided doses 1 to 6 times a day or in sustained release form.

13. A cosmetic composition for use in the treatment of at least one cosmetic condition of the keratinous tissue selected from the group consisting of acne scars, stretch marks, and wrinkles, the composition comprising an effective amount of at least one compound which must exhibit at least dual activity as a NF-KB signaling inhibitor and a Nrf2 signaling agonist in combination with at least one additional cosmetic additive, wherein the compound at least one structure selected from the group consisting of:
- stilbene which contains at least one substitute on at least one of the aryl rings;
- dienone; and
- 3-hydroxy-1,3-diphenylprop-2-en-1-one.

14. The composition of claim 13, wherein the cosmetic additive is selected from the group consisting of water, an alcohol or other water compatible cosmetically acceptable solvent, a water incompatible solvent, an emollient, a humectant, an oil, a conditioning agent, a surfactant, a thickener/thickening agent, a stiffening agent, an emulsifier, a medicament, a fragrance, a preservative, a deodorant component, an anti-perspirant compound, a skin protecting agent, a pigment, a dye, a coloring agent, a preservative or mixtures thereof.

15. The composition of claim 13, wherein the compound is included in an amount of 0.01-10 wt % of the composition.

16. The composition of claim 13, wherein the composition is a pharmaceutical composition and the compound is formulated in admixture with a pharmaceutically acceptable carrier.

17. The composition of claim 13, wherein the composition for direct skin application and is formulated in a lotion, cream, salve or liquid.

* * * * *